United States Patent
Fong

(10) Patent No.: US 9,471,181 B2
(45) Date of Patent: *Oct. 18, 2016

(54) LIGHT EMITTING DIODE SWITCH DEVICE AND ARRAY

(71) Applicant: Peter Sui Lun Fong, Monterey Park, CA (US)

(72) Inventor: Peter Sui Lun Fong, Monterey Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/482,909

(22) Filed: Sep. 10, 2014

(65) Prior Publication Data

US 2015/0084932 A1    Mar. 26, 2015

Related U.S. Application Data

(63) Continuation of application No. 13/011,745, filed on Jan. 21, 2011, now Pat. No. 8,866,708.

(51) Int. Cl.

| G09G 3/30 | (2006.01) |
| G09G 3/32 | (2016.01) |
| G06F 3/042 | (2006.01) |
| G06F 3/044 | (2006.01) |
| H05B 33/08 | (2006.01) |
| H01L 25/16 | (2006.01) |

(52) U.S. Cl.
CPC ............. *G06F 3/042* (2013.01); *G06F 3/044* (2013.01); *H05B 33/0863* (2013.01); *H01L 25/167* (2013.01); *H01L 2224/48091* (2013.01); *H01L 2224/48247* (2013.01); *H01L 2924/12041* (2013.01); *H01L 2924/19041* (2013.01); *Y02B 20/346* (2013.01)

(58) Field of Classification Search
CPC .......... H01L 2924/12041; H01L 2924/19041; H01L 25/167; G06F 3/044
See application file for complete search history.

(56) References Cited

U.S. PATENT DOCUMENTS

| 3,732,389 A | 5/1973 | Kaelin et al. |
| 4,054,814 A * | 10/1977 | Fegley .................. H01L 25/167 |
| | | 257/E25.032 |

(Continued)

FOREIGN PATENT DOCUMENTS

| CN | 1388501 | 1/2003 |
| DE | 3029595 | 10/1981 |
| DE | 3146328 | 6/1983 |

OTHER PUBLICATIONS

Elan Microelectronics Corp. "eKT2101 Capacitive Touch Pad Controller." Apr. 2008. (50 pages).

(Continued)

*Primary Examiner* — Michael J Eurice
(74) *Attorney, Agent, or Firm* — Stetina Brunda Garred and Brucker; Mark B. Garred

(57) ABSTRACT

An LED switch device and a matrix thereof are disclosed. There is an electroluminescent semiconductor element with a first polarity contact and a second polarity contact. There is also a first polarity LED lead frame, to which the electroluminescent semiconductor element is mounted. The first polarity contact of the electroluminescent semiconductor element is electrically connected to the first polarity LED lead frame. The LED switch device has a second polarity LED lead frame electrically connected to the second polarity contact of the electroluminescent semiconductor element. The LED switch device also has a touch sensor lead frame that is electrically connected to a touch sensor lead.

19 Claims, 23 Drawing Sheets

(56) References Cited

U.S. PATENT DOCUMENTS

| | | | | |
|---|---|---|---|---|
| 4,878,107 A * | 10/1989 | Hopper | .............. | H03K 17/941 |
| | | | | 220/2.1 R |
| 5,039,832 A * | 8/1991 | Polacek | .............. | H03K 17/18 |
| | | | | 200/317 |
| 5,343,064 A * | 8/1994 | Spangler | ........... | B81C 1/00246 |
| | | | | 257/350 |
| 5,638,052 A * | 6/1997 | Furuya | .................... | G09F 9/33 |
| | | | | 340/815.45 |
| 6,335,548 B1 | 1/2002 | Roberts et al. | | |
| 6,997,772 B2 | 2/2006 | Fong | | |
| 7,119,501 B2 | 10/2006 | Young | | |
| 2002/0056806 A1 * | 5/2002 | Bechtel | ................. | B60R 1/088 |
| | | | | 250/214.1 |
| 2002/0190326 A1 * | 12/2002 | Nagao | ................ | G09G 3/3648 |
| | | | | 257/359 |
| 2003/0168670 A1 * | 9/2003 | Roberts | ................ | B60Q 1/2665 |
| | | | | 257/98 |
| 2004/0118669 A1 * | 6/2004 | Mou | ........................ | H01H 9/12 |
| | | | | 200/310 |
| 2005/0077623 A1 * | 4/2005 | Roberts | ............ | H01L 23/49562 |
| | | | | 257/724 |
| 2005/0133810 A1 | 6/2005 | Roberts et al. | | |
| 2005/0184374 A1 | 8/2005 | Ohe et al. | | |
| 2006/0050032 A1 * | 3/2006 | Gunner | ............... | G09G 3/2077 |
| | | | | 345/82 |
| 2006/0086896 A1 * | 4/2006 | Han | ..................... | G06F 3/0421 |
| | | | | 250/221 |
| 2006/0262545 A1 * | 11/2006 | Piepgras | .................. | F21K 9/00 |
| | | | | 362/373 |
| 2006/0267049 A1 | 11/2006 | Tang et al. | | |
| 2007/0090543 A1 * | 4/2007 | Condie | .............. | H01L 23/3164 |
| | | | | 257/787 |
| 2008/0180390 A1 * | 7/2008 | Yoshikawa | ............ | G06F 3/044 |
| | | | | 345/156 |
| 2008/0230920 A1 * | 9/2008 | Behrens | ................. | H01L 24/05 |
| | | | | 257/777 |
| 2008/0238706 A1 | 10/2008 | Kenwright | | |
| 2009/0273570 A1 * | 11/2009 | Degner | ................... | G06F 3/044 |
| | | | | 345/173 |
| 2010/0177058 A1 * | 7/2010 | Lin | ........................ | G06F 3/044 |
| | | | | 345/174 |
| 2010/0193830 A1 * | 8/2010 | Lin | ...................... | H01L 21/486 |
| | | | | 257/99 |
| 2010/0321305 A1 * | 12/2010 | Chang | .................. | G06F 3/0412 |
| | | | | 345/173 |
| 2010/0328338 A1 * | 12/2010 | Kim | .................... | F21V 23/0442 |
| | | | | 345/589 |
| 2013/0341656 A1 * | 12/2013 | Chan | .................... | H01L 33/486 |
| | | | | 257/88 |
| 2014/0353694 A1 * | 12/2014 | Pang | ................... | H01L 25/0753 |
| | | | | 257/89 |

OTHER PUBLICATIONS

Sensacell. "Working with Sensacell." Dec. 2008. (5 pages).
Sensacell. "Sensacell Module-Model HS164-36-RGB." Jun. 2009 (5 pages).
International Search Report and Written Opinion for PCT/2012/020222. Apr. 25, 2012. (6 pages).
Chinese Office Action for Chinese Patent Application Serial No. 2012800144577, issued on Jun. 24, 2015. 13 pages.

* cited by examiner

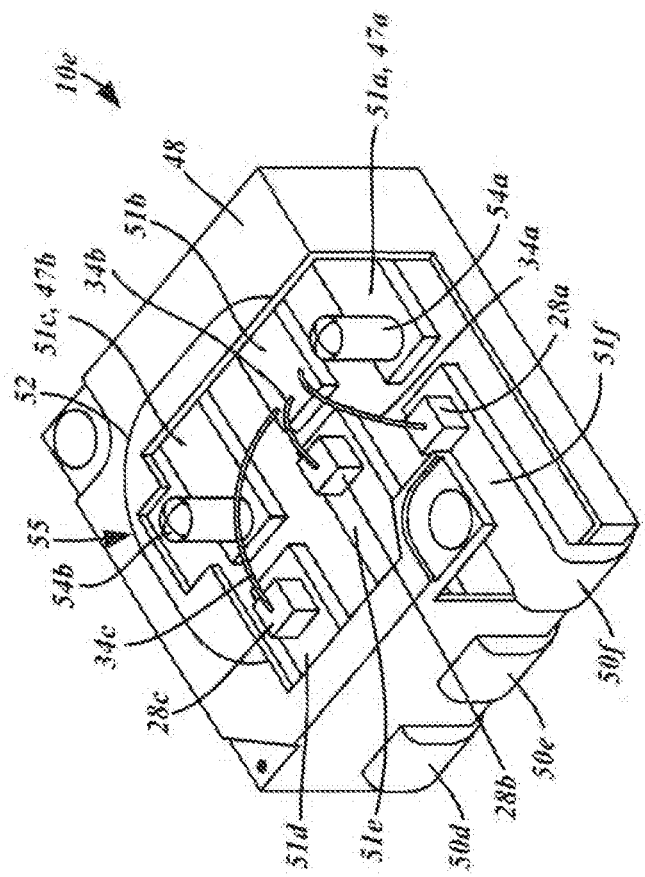
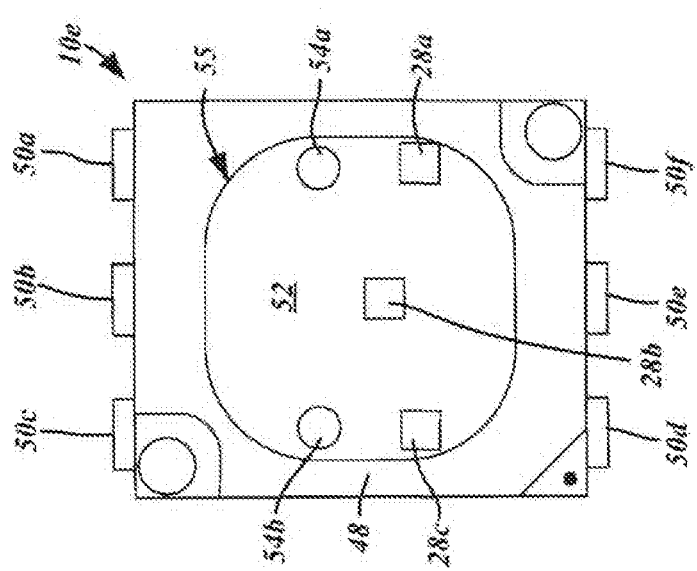
FIG. 6B
FIG. 6A

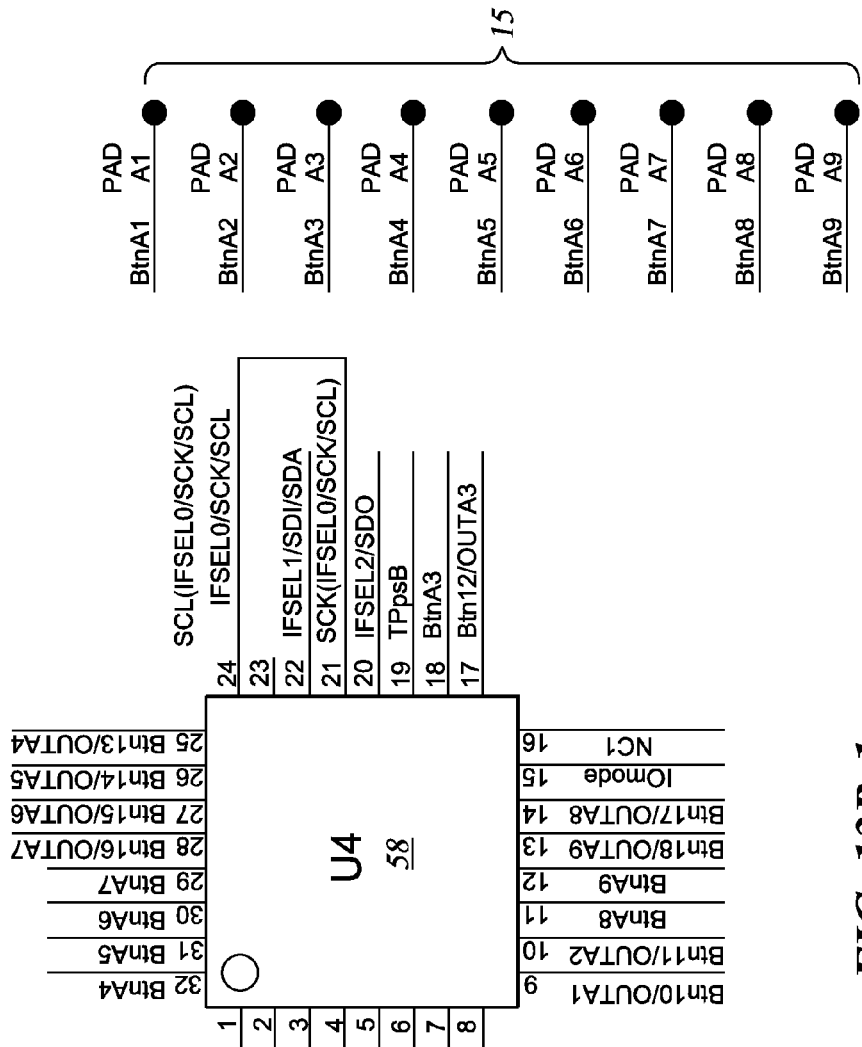
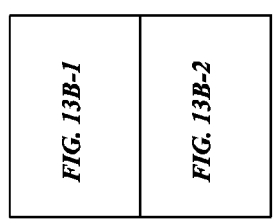
FIG. 13B
FIG. 13B-1

LIGHT EMITTING DIODE SWITCH DEVICE AND ARRAY

CROSS-REFERENCE TO RELATED APPLICATIONS

The present application is a continuation patent application of U.S. patent application Ser. No. 13/011,745, filed on Jan. 21, 2011 and now issued as U.S. Pat. No. 8,866,708, the entire content of which is wholly incorporated by reference herein.

STATEMENT RE: FEDERALLY SPONSORED RESEARCH/DEVELOPMENT

Not Applicable

BACKGROUND

1. Technical Field

The present disclosure relates generally to touch-sensitive electronic components and light emitting diodes (LEDs), and more particularly to an LED switch device and array.

2. Related Art

LEDs are ubiquitous output devices that find many applications across a variety of fields for their high efficiency, fast switching, and extended longevity, among other advantages. One of the most common utility is as indicators for electronic devices, and so LEDs are available in packages of different shapes and sizes to suit the particular application. Additionally, different illumination colors or radiation wavelengths across the visible spectrum are available, from the low wavelength red to the high wavelength violet. Several LEDs can be combined into arrays, with each LED being independently driven to generate visible patterns representative of text and graphics. Beyond the visible spectrum, however, there are LEDs capable of emitting infrared waves, which are typically utilized for inter-device communications. At the opposing end of the spectrum, ultraviolet waves may be utilized for sterilizing, sanitizing and disinfecting purposes. Although a typical miniature LED indicator light has an operating current of around 20 mA with less than 1 lumen of output, some recent high power LEDs are capable of operating currents of hundreds of mA and over a thousand lumens of output, which can serve as substitutes for incandescent bulbs in lighting applications.

The operational principles of LED devices are well known, with a central part being a semiconductor material that is doped to create a P-N junction. The anode, or the P-side of the junction is connected to a positive terminal of a power supply, while the cathode, or the N-side of the junction, is connected to a negative or common terminal of the power supply. As electricity flows between the P-N junction, energy in the form of a light photon is released. Whether utilized as a miniature, low power indicator or as a high-intensity illuminator, LEDs operate in this manner. In some applications, an LED can be utilized as a photodetector, where photons of light falling on the P-N junction are converted to an electrical signal. Instead of being connected to a power supply, the LED may be connected to a detection circuit to produce a response upon receiving a signal therefrom.

Except in the aforementioned application as a photodetector, packaged LED devices are generally considered basic output devices. As noted, an array of LEDs can be devised with each one being controlled individually in order to generate coherent visual patterns. Direct user interactions with such visual outputs over display arrays have been contemplated, but such devices have involved a separate input device that is overlaid on the output device. One example is a capacitive touch screen utilized in slate computing devices such as TabletPCs from various manufacturers and the iPad® from Apple, Inc. of Cupertino, Calif.

These devices are known to utilize a transparent or semi-transparent sensor panel comprised of rows and columns of traces on opposite sides of a dielectric. The traces are comprised of indium tin oxide or antimony tin oxide, with a top glass panel being etched with the column traces and a bottom glass panel being etched with the row traces. For the touch sensor panel to be transparent, the etched traces are around 30 microns. Separating the top glass panel and the bottom glass panel may be a transparent polymer spacer that serves as the dielectric between the column traces and the row traces. The sensor panels are then mounted in an overlapping relationship to the liquid crystal display (LCD).

Another example of incorporating simultaneous input and output capabilities in displays, albeit on a slightly larger scale, are LED matrices with switches close to the LEDs. One known device is disclosed in U.S. Pat. No. 5,638,052 to Furuya, et al, which discloses an array of LEDs with switches for turning on or turning off individual LEDs being provided at locations corresponding to or close to the LEDs. The Sensacell device produced by Sensacell Inc. of Brooklyn, N.Y. is similar to the Furuya, et al. device, except for the use of capacitive sensors disposed amongst a matrix of LEDs each forming a unit of inter-connectible cells.

In these earlier systems, the output or display device is configured independently from the input device. Accordingly, there is a need in the art for an integrated LED switch device and array.

BRIEF SUMMARY

In accordance with various embodiments of the present disclosure, an LED switch device is contemplated. There may be an electroluminescent semiconductor element with a first polarity contact and a second polarity contact. The LED switch device may have a first polarity lead frame, to which the electroluminescent semiconductor element is mounted. The first polarity contact of the electroluminescent semiconductor element may be electrically connected to the first polarity lead frame. Additionally, there may be a second polarity lead frame that may be electrically connected to the second polarity contact of the electroluminescent semiconductor element. There may also be a touch sensor lead frame that may be electrically connected to a touch sensor lead.

Another embodiment of the present disclosure may be a light emitting diode switch device. The device may include a first polarity lead. Additionally, there may be at least one electroluminescent semiconductor element that has a first polarity contact and a second polarity contact. The device may further include a first polarity LED lead frame with the at least one electroluminescent semiconductor element mounted thereto. The first polarity contact thereof may be electrically connected to the first polarity lead. There may also be a second polarity lead, as well as a second polarity LED lead frame that is electrically connected to the second polarity lead. The second polarity LED lead frame may be electrically connected to the second polarity contact of the electroluminescent semiconductor element. There may also be a first touch sensor lead, as well as a touch sensor lead frame to which it is electrically connected. The second polarity lead may be connectible to a light emitting diode driver source. The touch sensor lead may be connectible to a touch sensor controller input.

According to yet another embodiment of the present disclosure, there is a combination input and output device. The device may include a light emitting diode driver integrated circuit that has a plurality of independent output lines. Additionally, there may be a touch input controller integrated circuit that has a plurality of independent input lines. The device may also include an array of light emitting diode switch devices. The light emitting diode switch device, in turn, may include a first electroluminescent semiconductor element electrically connected to a one of the plurality of independent output lines of the light emitting diode driver integrated circuit. The light emitting diode switch device may further include a first integrated touch sensor lead electrically connected to a one of the plurality of independent input lines of the touch input controller. The first electroluminescent semiconductor element and the first integrated touch sensor lead may be encapsulated into a case.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which:

FIG. 6A is a top plan view of a fifth embodiment of the LED switch device with a surface mount device (SMD) package;

FIG. 6B is a perspective view of the SMD package LED switch device shown in FIG. 6A with a cutout view showing selected internal portions thereof;

FIGS. 13A-1, 13A-2, 13B-1 and 13B-2 are detailed schematic diagrams of a circuit of the remote controller depicted in FIG. 12;

FIGS. 19A-1, 19A-2, 19B-1, 19B-2, and 19C are detailed schematic diagrams of a circuit of the interactive doll;

Common reference numerals are used throughout the drawings and the detailed description to indicate the same elements.

DETAILED DESCRIPTION

The present disclosure contemplates a light emitting diode (LED) switching device and array. The detailed description set forth below in connection with the appended drawings is intended as a description of the several presently contemplated embodiments of these devices, and is not intended to represent the only form in which the disclosed invention may be developed or utilized. The description sets forth the functions and features in connection with the illustrated embodiments. However, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figures 1, 2:
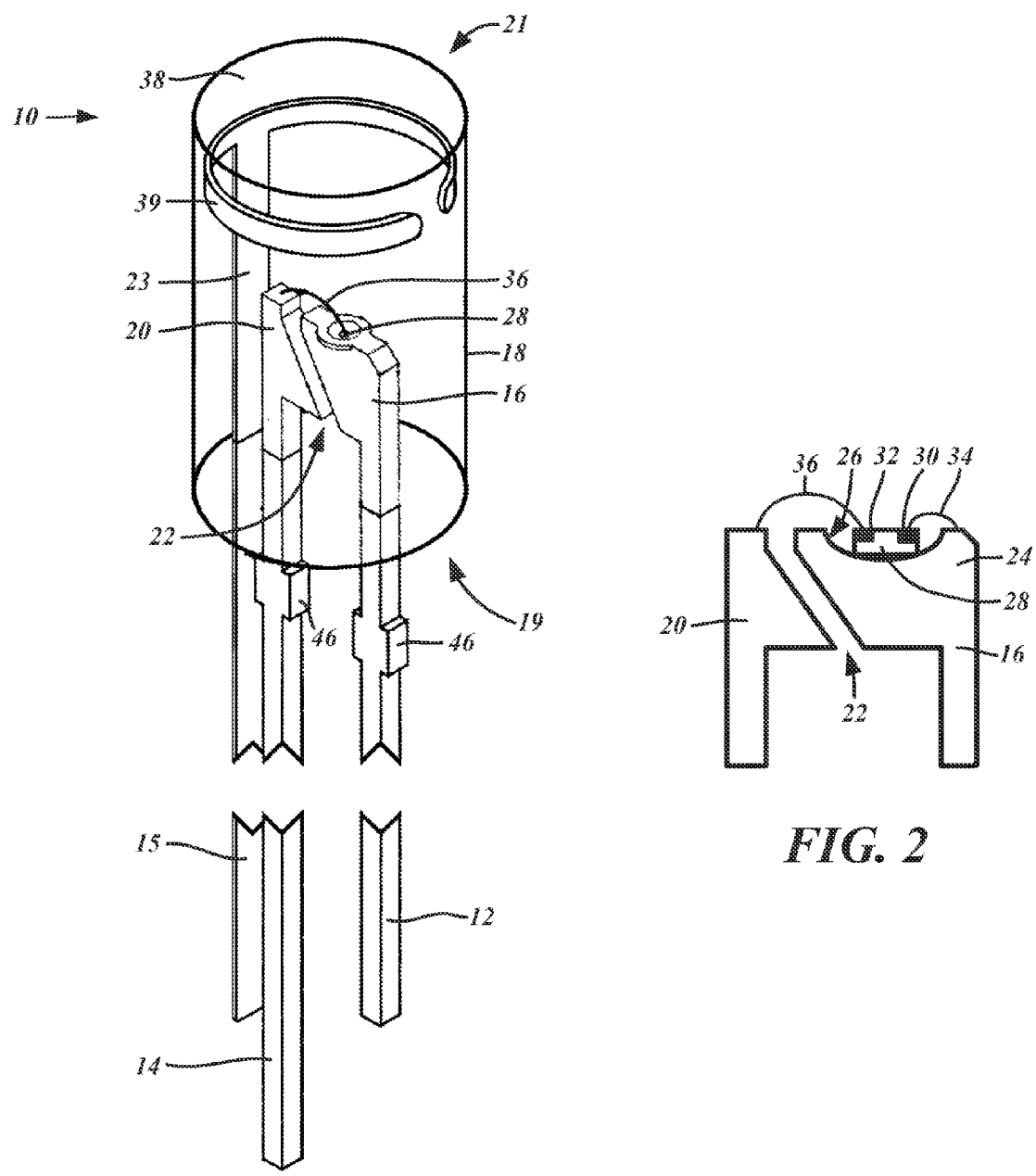
FIG. 1 is a perspective view of an LED switch device in accordance with various embodiments of the present disclosure.
FIG. 2 is a cross sectional view of an electroluminescent semiconductor die mounted to a lead frame.

FIG. 1 illustrates one embodiment of a presently contemplated LED switch device 10, which includes a first polarity lead 12, a second polarity lead 14, and a touch sensor lead 15. LEDs in general and the LED switch device 10 in particular can have a common-cathode or a common-anode configuration. In a common cathode configuration, the first polarity lead 12 corresponds to a cathode while the second polarity lead 14 corresponds to an anode. In a common anode configuration, the first polarity lead 12 corresponds to an anode while the second polarity lead 14 corresponds to a cathode.

Although the embodiments disclosed herein have a common cathode configuration, it will be appreciated by those having ordinary skill in the art that the contemplated features are also applicable in a common anode configuration. Along these lines, although various features are described as being particular to an anode or a cathode, the use of these terms is for purposes of consistency with respect to the examples presented. For example, the first polarity leads 12 are referred to as cathode leads in a common-cathode configuration, but in a common-anode configuration, the first polarity leads 12 may be appropriately referenced as anode leads. Further, the use of the term anode or cathode as modifiers of various components are likewise not intended to be limiting, particularly with respect to the direction of current flow as would be suggested by the use of such terms. Thus, the term anode could refer to an electrode through which electrical current enters the LED switch device 10, as well as an electrode through which electrical current exits the LED switch device 10.

The first polarity/cathode lead 12 is structurally contiguous with a first polarity/cathode lead frame anvil 16, both of which are electrically conductive. The cathode lead frame anvil 16 is embedded within a case 18, which has a generally cylindrical configuration with a bottom end 19 and an opposed top end 21. In further detail, the cathode lead frame anvil 16 may be enlarged, that is, thicker and/or wider, in comparison to the cathode lead 12 for rigidity and support. A part of the cathode lead 12 are also embedded within the case 18, while other portions extend from the bottom end 19 of the case 18.

Also embedded within the case 18 is a second polarity/anode lead frame post 20, which is structurally contiguous with the second polarity/anode lead 14. Like the cathode lead 12 and the cathode lead frame anvil 16, the anode lead 14 and the anode lead frame post 20 are electrically conductive. The cathode lead frame anvil 16 is structurally independent of the anode lead frame post 20, and there is an oblique gap 22 of varying sizes and shapes defined between. Although the terms "anvil" and "post" are used to reference certain features of the lead frames in the LED switch device 10, it will be recognized that this is for purposes of convenience in differentiating between several features and not in any limiting sense. For instance, the anvil may also be referred to as a first polarity LED lead frame, and the post may also be referred to as a second polarity LED lead frame. In some cases, the correspondence of terminology may be reversed. Those having ordinary skill in the art will understand that similar features, whether referred to as anvils, posts, or by any other term, refers to the same basic structure described herein.

Another component embedded within the case 18 is a touch sensor lead frame 23, which is structurally contiguous with the touch sensor lead 15. Again, like the other leads, lead frame posts, and lead frame anvils discussed above, the touch sensor lead 15 and the touch sensor lead frame 23 are electrically conductive. The anode lead 14 and the touch sensor lead 15 also extend from the bottom end 19 of the case 18. In some contemplated embodiments, the touch sensor lead 15 may be configured similarly to the anode lead 14 except for the pertinent features thereof that will be discussed more fully below. The touch sensor lead frame 23 may be configured similarly to the anode lead frame post 20, in that there are no electroluminescent semiconductor dies 28 mounted thereon. Indeed, in these embodiments, these components may be a repurposed anode lead 14 and anode lead frame post 20.

With additional reference to FIG. 2, a top portion 24 of the cathode lead frame anvil 16, which faces the top end 21 of the case 18, defines a die mounting crater 26. In accordance with various embodiments of the LED switch device 10, an electroluminescent semiconductor die 28 is attached to the cathode lead frame anvil 16 and in particular disposed within the die mounting crater 26. In some configurations, the die mounting crater 26 has a reflective surface, though this is optional. The electroluminescent semiconductor die 28 has a first polarity/cathode contact 30, and a second polarity/anode contact 32. As discussed above, the electroluminescent semiconductor die 28 has a P-N junction from which photons of light are emitted at a particular wavelength as electrons flows through holes therein as the energy level is lowered. Thus, the cathode contact 30 is the negative electrode, while the anode contact 32 is the positive electrode. It is understood that the emitted wavelength or color may be varied by changing the material of the P-N junction, specifically based upon its band-gap energy.

FIG. 2 illustrates the electroluminescent semiconductor die 28 being mounted directly onto the cathode lead frame anvil 16. The electrical connection to the N-side electrode of the P-N junction, however, is made through the cathode contact 30 and a first wire bond 34. It is also known to connect the cathode contact 30 directly to the cathode lead frame anvil 16.

As indicated above, the LED switch device 10 in accordance with various embodiments includes a plurality of second polarity/anode lead frame posts 20. The first anode lead frame post 20a, otherwise referred to as an LED lead frame post because of its function, is electrically connected to the anode contact 32 of the electroluminescent semiconductor die 28, and hence the P-side electrode of the P-N junction, over a second wire bond 36. Thus, the circuit from the anode lead 14 and the anode lead frame post 20, to the electroluminescent semiconductor die, to the cathode lead frame anvil 16 and the cathode lead 12 is completed.

The mounting orientation and the surface of the electroluminescent semiconductor die 28 may be optimized for reflecting the maximum amount of light in one or more desired directions. In this regard, because the top end 21 of the case 18 is the typical emission direction, the electroluminescent semiconductor die 28 is oriented thus. For additional focusing of the emitted light, the case 18 may include a lens 38 that focuses the emitted light. In further detail, it is contemplated that the case 18 is constructed of a transparent or at least translucent epoxy material that may be colored to match that of the emitted light.

Although a single electroluminescent semiconductor die 28 that emits one color is shown in FIG. 1 and FIG. 2, it will be recognized that any number of additional ones may be included in the LED switch device 10. Generally, a first one of the electroluminescent semiconductor dies 28 may correspond to a first visible spectrum wavelength emission, and a second one of the electroluminescent semiconductor dies 28 may correspond to a second visible spectrum wavelength emission, where the first emitted wavelength is different than the second emitted wavelength. In one exemplary embodiment, the electroluminescent semiconductor dies for the colors red, green, and blue may be incorporated into the LED switch device 10 to generate different hues of light that are combinations of these primary colors.

Referring again to FIG. 1, the LED switch device 10 includes the touch sensor lead frame 23 that is structurally independent of the anode lead frame post 20 and electrically isolated from the same. Furthermore, the touch sensor lead frame 23 may be connected to the touch sensor lead 15. The touch sensor lead frame 23 may be disconnected from the electroluminescent semiconductor die 28. While it is possible to mount an electroluminescent semiconductor die 28 to the touch sensor lead frame 23, so long as the circuit therefor is not completed, i.e., there are no connections to a power source and/or to ground, it is understood that such electroluminescent semiconductor die will remain largely non-functional.

The touch sensor lead frame 23 is connected to a touch sensor contact 39 that is contemplated to serve as an electrode for measuring body capacitance. It is understood the human body in general, and appendages thereof such as fingers in particular, typically have a capacitance of around 22 pF. As will be discussed in further detail below, the capacitance thus detected by the touch sensor contact 39 can be ascertained using additional input control circuitry per various modalities known in the art. Thus, as a finger is pressed against or moved into the proximity of the surface of the case 18, the capacitance detected on the touch sensor contact 39 changes, with this input being usable for triggering additional functionality. In accordance with the embodiment of the LED switch device 10 shown in FIG. 1, the touch sensor lead frame 23 is extended further towards the top end 21 of the case 18. The touch sensor contact 39 is embedded within the case 18 and extends substantially around the circumference of the same, and is connected to the touch sensor lead frame 23. As such, it is envisioned that a finger placed on or placed in the proximity of any portion of the lens 38 is detectable.

Figure 3A:
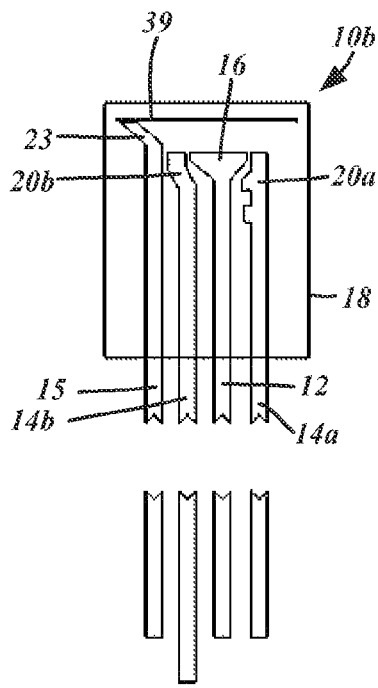
FIG. 3A is a side view of a second embodiment of the LED switch device with an additional electroluminescent semiconductor die.
Figure 3B:
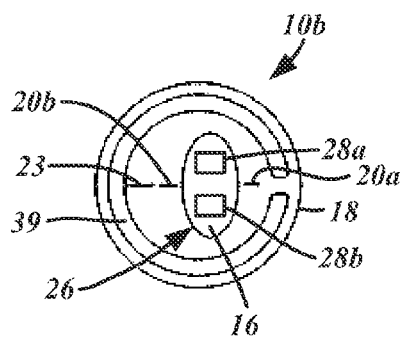
FIG. 3B is a top view of the second embodiment of the LED switch depicted in FIG. 3A.

Several different variations of the LED switch device 10 are contemplated. With reference to FIG. 3A and FIG. 3B, a second embodiment of the LED switch device 10b includes an alternatively shaped cathode lead frame anvil 16, which is structurally contiguous with the cathode lead 12. Attached to the die mounting crater 26 is a first electroluminescent semiconductor die 28a and a second electroluminescent semiconductor die 28b. As briefly indicated above, emitting a plurality of different colors/wavelengths from the single LED switch device 10 is possible by adding another LED element. In this particular example, the first electroluminescent semiconductor die 28a may emit a red color wavelength light, while the second electroluminescent semiconductor die 28b may emit either a green or blue color wavelength light. For separate control of these electroluminescent semiconductor dies 28a, 28b, amongst the first subset of anode lead frame posts 20, there is a first one 20a that is electrically connected to the first electroluminescent semiconductor die 28a over a wire bond and a second one 20b that is electrically connected to the second electroluminescent semiconductor die 28b also over a wire bond. The first anode lead frame post 20a is structurally contiguous with the first anode lead 14a, while the second anode lead frame post 20b is structurally contiguous with a corresponding second anode lead 14b.

As with the first embodiment of the LED switch device 10 discussed above, the second embodiment 10b includes the touch sensor lead frame 23 that is connected to the one touch sensor contact 39. Again, the touch sensor lead frame 23 is structurally contiguous with the touch sensor lead 15. The touch sensor contact 39 is disposed toward the top end 21 of the case 18, and defines a partial loop around its circumference. Furthermore, each of the aforementioned components are embedded within a transparent or at least translucent case 18.

Figure 4A:
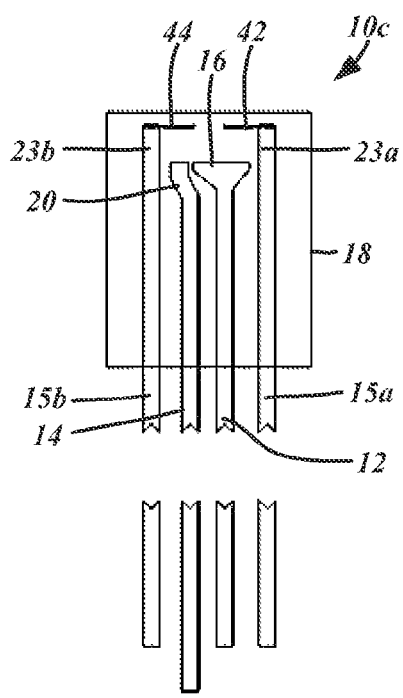
FIG. 4A is a side view of a third embodiment of the LED switch device including a pair of touch sensor contacts.
Figure 4B:
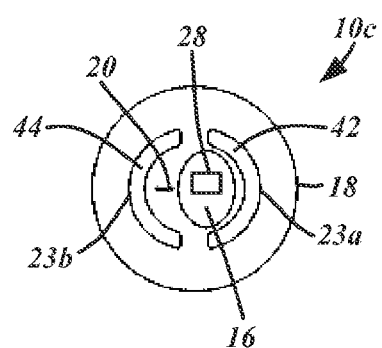
FIG. 4B is a top view of the third embodiment of the LED switch device shown in FIG. 4A.

A third embodiment of the LED switch device 10c is shown in FIGS. 4A and 4B. Similar to the previously described embodiments, there is the cathode lead frame anvil 16 that is structurally contiguous with the cathode lead 12. Again, attached to the die mounting crater of the cathode lead frame anvil 16 is the electroluminescent semiconductor die 28. Since there is only one electroluminescent semiconductor die 28, only a single color wavelength is emitted, and is driven by an electrical current delivered to the single anode lead frame post 20, which is structurally contiguous with the anode lead 14.

Instead of a single touch sensor contact 39, the third embodiment of the LED switch device 10c contemplates two separate ones that are alternatively configured. In further detail, a first touch sensor contact 42 has a semicircular configuration and extends inwardly towards the center axis of the case 18. Additionally, a second touch sensor contact 44 is laterally opposite the first touch sensor contact 42 but has the same semicircular configuration and extends inwardly towards the center axis of the case 18. The first touch sensor contact 42 is structurally contiguous with a first touch sensor lead frame 23a as well as a first touch sensor lead 15a. The second touch sensor contact 44, in turn, is structurally contiguous with the second touch sensor lead frame 23b and the second touch sensor lead 15b. There being two separate touch sensor contacts 42, 44, it is understood that any touch inputs can be separately or simultaneously registered, thereby providing an additional degree of precision.

Figure 5A:
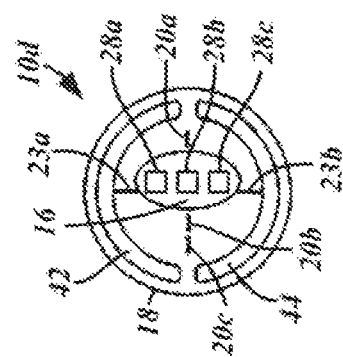
FIG. 5A is a side view of a fourth embodiment of the LED switch device including a pair of touch sensor contacts and multiple electroluminescent semiconductor dies.
Figure 5B:
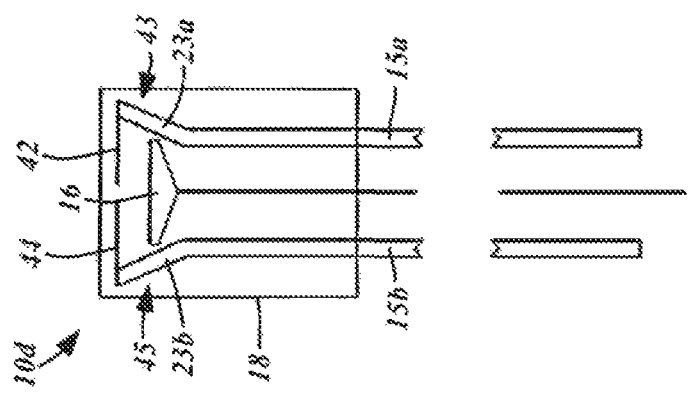
FIG. 5B is a front view of the fourth embodiment of the LED switch device depicted in FIG. 5A.
Figure 5C:
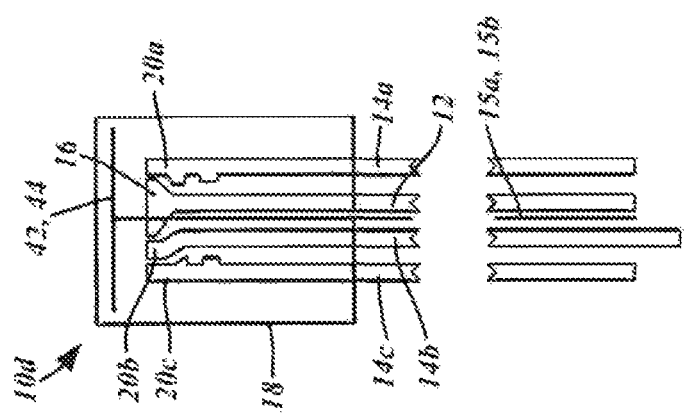
FIG. 5C is a top plan view of the fourth embodiment of the LED switch device depicted in FIGS. 5A and 5B.

With reference to FIGS. 5A, 5B, and 5C, a fourth embodiment of the LED switch device 10d includes the cathode lead frame anvil 16, on which a first electroluminescent semiconductor die 28a, a second electroluminescent semiconductor die 28b, and a third electroluminescent semiconductor die 28c are mounted. In this embodiment, it is contemplated that the full color spectrum is reproducible using the primary colors of red, green, and blue, so these three electroluminescent semiconductor dies 28a-c correspond thereto. The cathode lead frame anvil 16 is structurally contiguous with the cathode lead 12. The electroluminescent semiconductor dies 28a-c are independently controllable, as will be described below.

As best illustrated in FIG. 5A, there is a first anode lead frame post 20a that is structurally contiguous with the first anode lead 14a. Additionally, there is a second anode lead frame post 20b that is structurally contiguous with the second anode lead 14b, as well as a third anode lead frame post 20c that is structurally contiguous with the third anode lead 14c. It is understood that the first anode lead frame post 20a, the second anode lead frame post 20b, and the third anode lead frame post 20c are electrically connected to a respective one of the first electroluminescent semiconductor die 28a, the second electroluminescent semiconductor die 28b, and a third electroluminescent semiconductor die 28c over individual wire bonds. The anode lead frame posts 20 are oriented along a single lateral axis.

FIG. 5B and FIG. 5C best illustrate a first touch sensor lead frame 23a and a second touch sensor lead frame 23b that are oriented in a perpendicular relationship to the anode lead frame posts 20 described above. However, it is possible for these touch sensor lead frames 23 to be oriented along a single lateral axis as the anode lead frame posts 20. The first touch sensor lead frame 23a is structurally contiguous with a first touch sensor lead 15a as well as the first touch sensor contact 42. The second touch sensor lead frame post 23b is structurally contiguous with a second touch sensor lead 15b and the second touch sensor contact 44. Like the third embodiment of the LED switch device 10c described above, the first touch sensor contact 42 has a semicircular configuration that is opposed to the second touch sensor contact 44, which also has a semicircular configuration. The first touch sensor lead frame post 23a has a bent section 43 that extends the coverage area of the first touch sensor contact 42. The second touch sensor lead frame post 23b similarly has a corresponding bent section 45 for extending the second touch sensor contact 44 toward the outer portion of the case 18.

As can be seen from the forgoing examples, the LED switch device 10 can be configured in numerous ways, particularly with respect to the configuration of electroluminescent semiconductor dies 28 and the touch sensor contact 39 or touch sensor contacts 42, 44. These examples are not intended to be limiting, and based upon a proper understanding of the present disclosure, those having ordinary skill in the art will be capable of developing further alternatives.

The foregoing examples are all configured as throughhole cylindrical packages suitable for installation on conventional printed circuit boards. With reference again to FIG. 1, the leads 12, 14 include stop tabs 46 that limit the extent of insertion into the holes on the printed circuit board. However, it will be appreciated that the features of the LED switch device 10 can be incorporated into any package shape including round dome top, round flat top, rectangular flat top, triangular or square flat top, and so forth. Among these different shapes, various sizes are also possible. Likewise, the orientation of the touch sensor contacts 42, 44 as well as the various leads, including the first polarity lead 12, the second polarity lead 14, and the touch sensor lead 15 may extend from the case 18 in various directions, such as from the side, at an angle, and so forth. Those having ordinary skill in the art will appreciate that the specific form factors presented are by way of example, and based upon the features disclosed in the context of such specific form factors, the features may be readily implemented in alternative form factors, whether presently known or unknown.

As best shown in FIGS. 6A and 6B, another embodiment of the LED switch device 10e contemplates the use of a surface mount device (SMD) package. More particularly, there is a carrier 48 with leads 50a-50f extending therefrom for connecting to external components. In the illustrated embodiment, there is the first electroluminescent semiconductor die 28a with a first illumination color, the second electroluminescent semiconductor die 28b with a second illumination color, and the third electroluminescent semiconductor die 28c with a third illumination color. The sixth lead 50f is structurally contiguous and electrically common with a sixth lead frame 51f, on which the first electroluminescent semiconductor die 28a is mounted, and to which it is electrically connected. The fifth lead 50e is structurally contiguous and electrically common with a fifth lead frame 51e, on which the second electroluminescent semiconductor die 28b is mounted, and to which it is electrically connected. Furthermore, the fourth lead 50d is structurally contiguous and electrically common with a fourth lead frame 51d, on which the third electroluminescent semiconductor die 28c is mounted, and to which it is electrically connected. The second lead 50b is structurally contiguous and electrically common with a second lead frame 51b, which serves as a common anode for the electroluminescent semiconductor dies 28a-c. The anodes of each of the electroluminescent semiconductor dies 28a-c is electrically connected to the second lead frame 51b over respective wire bonds 34a-c, while the contacts with the lead frames 51d, 51e and 51f, respectively, are made on the cathodes of the electroluminescent semiconductor dies 28a-c by means of a conductive adhesive.

The LED switch device 10e also includes the first touch sensor contact 54a that is mounted to and electrically common with a first lead frame 51a, also referred to as a first touch sensor lead frame 47a. The third lead 50c is understood to be structurally contiguous with the third lead frame 51c. Additionally, the second touch sensor contact 54b is mounted to and electrically common with a third lead frame 51c, also referred to as a second touch sensor lead frame 47b. The third lead frame 51c is structurally contiguous with the third lead 50c. The size, shape and general configuration or form factor of the touch sensor contacts 54 and touch sensor lead frames 47 employed in the LED switch device 10e are presented by way of example only, and may be differently configured than as shown in FIG. 6B.

The carrier 48 may encapsulate portions of the various lead frames 51a-f, and the electroluminescent semiconductor dies 28a-28c are disposed within the same. The carrier 48, however, defines an opening 55 through which the touch sensor contacts 54 and/or the electroluminescent semiconductor dies 28 are exposed. There is a transparent or partially translucent case 52 that encapsulates such components. In some embodiments of the SMD package, portions or the entirety of the touch sensor contacts 54 may be encapsulated within the carrier 48, and may not be exposed through the case 52. It will be appreciated that although the structural design and form factor of a specific surface mount package has been shown and described, other structural designs and form factors of surface mount packages may be utilized.

Figure 7:
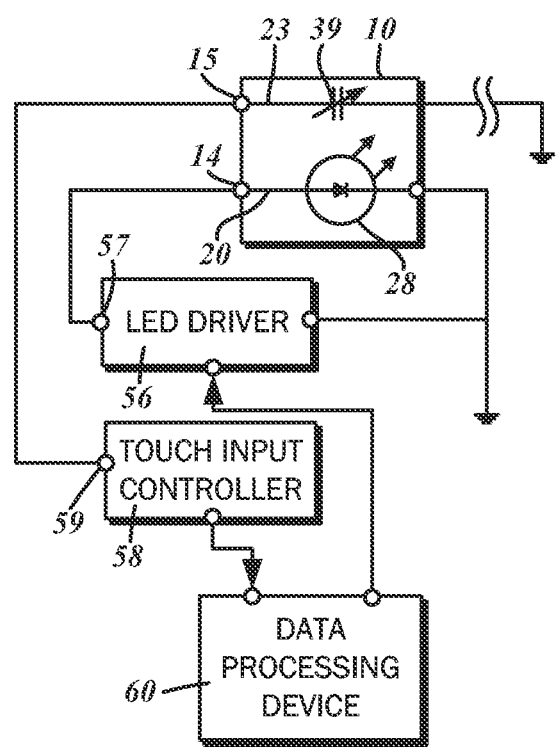
FIG. 7 is a block diagram illustrating a basic application utilizing the LED switch device in connection with an LED output driver and a touch input controller.

Having considered the basic parts of several embodiment of the LED switch device 10, one exemplary use thereof will now be described. With reference to the block diagram of FIG. 7, the LED switch device 10 is connected to an LED driver 56 as well as a touch input controller 58. In one embodiment, the touch input controller 58 is the eKT2101 capacitive touch pad controller integrated circuit from Elan Microelectronics Corp. of Hsinchu, Taiwan. It is understood that the LED driver 56 generates an electrical signal on an output line 57 that is transmitted through the anode lead 14 and the anode lead frame post 20, activating the electroluminescent semiconductor die 28 in accordance with conventional techniques. Additionally, it is understood that an input line 59 of the touch input controller 58 is connected to the touch sensor lead 15 and the touch sensor lead frame 23, with the touch input, that is, the corresponding capacitance change on the touch sensor contact 39, being detected. Though further details will follow, the output from the LED driver 56 can be initiated by a data processing device 60 or controller. Furthermore, the touch input controller 58 can generate a data signal indicative of a touch input upon detection thereof, and that data signal can be transmitted to the data processing device 60. Based on such touch inputs and possibly other types of inputs, appropriate responses to the LED driver 56 can be generated.

Figure 8B:
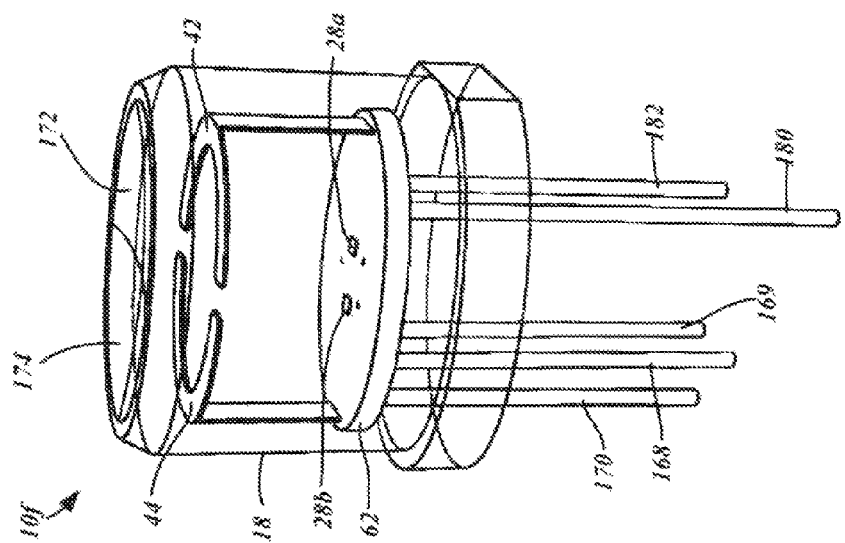
FIG. 8B is a perspective view of the sixth embodiment of the LED switch device shown in FIG. 8A.
Figure 8A:
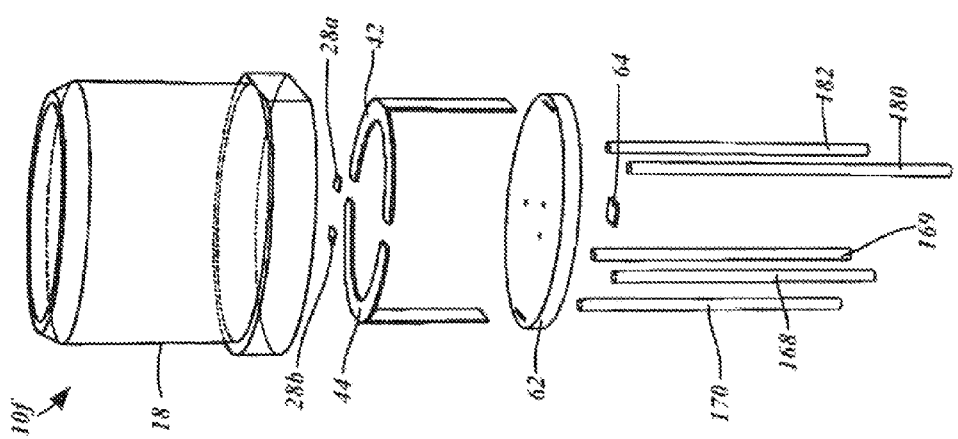
FIG. 8A is an exploded perspective of a sixth embodiment of the LED switch device with the touch input controller embedded therein.

In the embodiment discussed above, the touch input controller 58 is understood to be separate from the LED switch device 10. However, as illustrated in FIG. 8A and FIG. 8B, yet another embodiment of the LED switch device 10f includes an embedded printed circuit board 62 with an LED switch device controller integrated circuit 64 mounted thereto. It is contemplated that the LED switch device controller integrated circuit 64 incorporates the functionality of the LED driver 56, the touch input controller 58, and the data processing device 60 into a single package. Like the other variations, the first electroluminescent semiconductor die 28a and the second electroluminescent semiconductor die 28b are embedded within the case 18, though they are mounted to the printed circuit board 62.

A power lead 180 and the ground lead 182 are attached to the printed circuit board 62, and are understood to supply power/ground to the LED switch device 10f. In particular, power and ground connections of the LED switch device controller integrated circuit 64 are in electrical communication with the power lead 180 and the ground lead 182. Power to drive the touch input controller 58, the LED driver 56, and the data processing device 60 is understood to be supplied thereby.

As noted above, the first touch sensor contact 42 and the second touch sensor contact 44 are electrodes that are utilized for detecting capacitance changes, and in and of themselves do not generate signals that are typical of data transmissions for the data processing device 60. The LED switch device controller integrated circuit 64 is understood to detect the capacitance change. In the LED switch device 10*f*, there are understood to be two electrodes, the first touch sensor contact 42 and the second touch sensor contact 44, which are connected to independent inputs of the LED switch device controller integrated circuit 64.

The LED switch device 10*f* has two outputs, that is, a first output lead 168 and a second output lead 169. A signal indicating that the first touch sensor contact 42 was activated can be generated on the first output lead 168, while another signal indicating that the second touch sensor contact 44 was activated can be generated on the second output lead 169. With the functionality of the data processing device 60 embedded into the LED switch device 10*f*, other outputs besides such a simple indicator directly tied to the touch input controller 58 may be generated. In other words, the output generated at the output leads 168, 169 may be independent of the inputs detected by the touch sensor contacts 42, 44. As will be described in further detail below, the touch input as detected by the touch input controller 58 may be further processed to control various external devices. Thus, it is expressly contemplated that additional output leads may be provided.

In addition to the two outputs, the LED switch device 10*f* also has an input lead 170, through which various external inputs may be connected. The inputs received may be utilized to control the lighting of the electroluminescent semiconductor devices 28*a*, 28*b*, though again, because of the incorporation of the functionality of the data processing device 60, more sophisticated responses beside an activation or a deactivation may be generated, such as dimming, color mixing, flashing, and so forth.

Because touching one of the first touch sensor contact 42 or second touch sensor contact 44 generates a different response from the LED switch device controller integrated circuit 64, additional visual segregation thereof is contemplated. The top end 21 of the case 18 has a concave surface with an oval outline that is divided into a first segment 172 and a second segment 174. Thus, touching the first segment 172 is understood to trip the first touch sensor contact 42 that results in an output being generated on the first output lead 168, while touching the second segment 174 trips the second touch sensor contact 44 with an output generated on the second output lead 169. Touching both the first segment 172 and the second segment 174 simultaneously may result in an output on both the first output lead 168 and the second output lead 169. For the most part, the output from the two electroluminescent semiconductor dies 28 are independent of any touch input, as they are separately controlled from a data processing device 60 in response to the touch input.

Although simple on/off functionality is described herein, it will be appreciated by those having ordinary skill in the art that a finer degree of receptiveness to touch input is possible, such as partial placement, swiping from one to the other, and so forth. Variations on the incorporation of multiple functions into the single package of the LED switch device 10 are understood to be within the purview of those having ordinary skill in the art.

Figure 9:
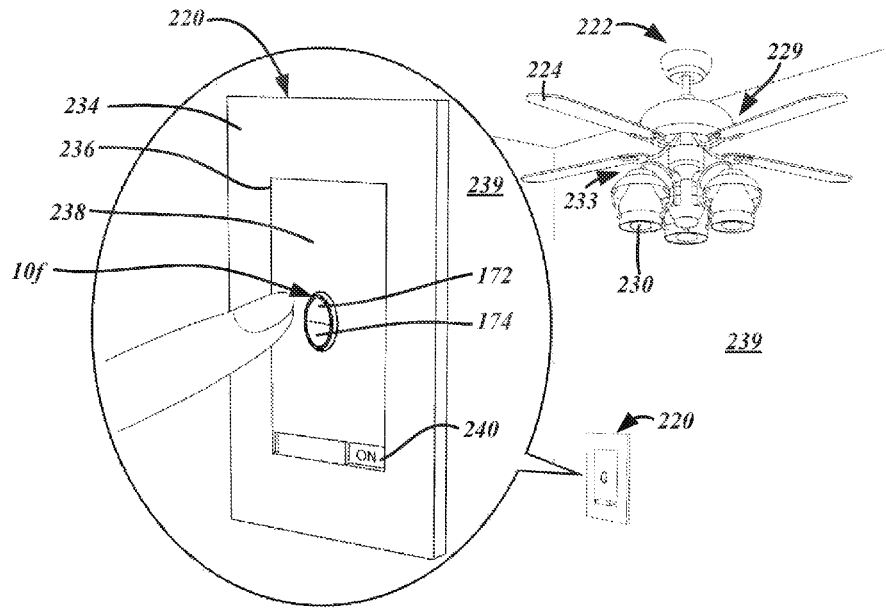
FIG. 9 is a perspective view of a control switch and a ceiling fan light fixture controlled thereby, with the control switch utilizing the sixth embodiment of the LED switch device shown in FIG. 8A and FIG. 8B being enlarged.
Figure 10:
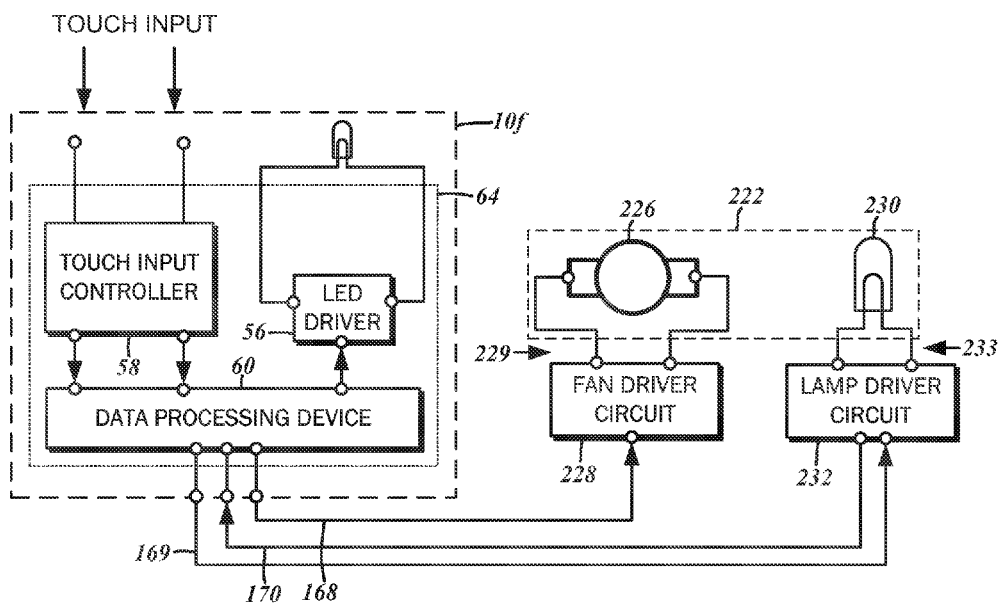
FIG. 10 is a block diagram showing the sixth embodiment of the LED switch device configured to control the ceiling fan light fixture as shown in FIG. 9.

As will become apparent, the LED switch device 10 and its different configurations may be utilized in a wide variety of applications. With reference to FIG. 9, the aforementioned LED switch device 10*f* may be utilized as a wall-mounted control switch 220, to control the various functions of a ceiling fan light fixture 222. Referring additionally to the block diagram of FIG. 10, the ceiling fan light fixture 222 includes fan blades 224 spun by an electric motor 226. Due to the high current requirements to drive the electric motor 226, there is a fan driver circuit 228 that draws power separately from an external source. Along these lines, the ceiling fan light fixture 222 includes lamps 230 that illuminates the room upon activation. Like the electric motor 226, the lamps 230 have higher current/power requirements than that which can be supplied by the LED switch device 10*f*, so there is lamp driver circuit 232 that draws power from an external source. The fan driver circuit 228 and the lamp driver circuit 232 are controlled by the LED switch device 10*f* based upon the inputs received thereon, and can include rotation speed changes (fast, medium, slow) of the fan blades 224, as well as the intensity/dimming level of the lamps 230. Feedback that indicates the actual lighting level of the lamps 230 can also be generated by the lamp driver circuit 232 back to the LED switch device 10*f*. The fan blades 224, the electric motor 226, and the fan driver circuit 228 will be collectively referenced as a fan unit 229, while the lamps 230 and the lamp driver circuit 232 will be collectively referenced as a lamp unit 233. It will be recognized that the fan unit 229 and the lamp unit 233 may include further additional components, however.

The control switch 220 includes a conventional wall panel 234, within which a receptacle 236 is defined. An LED switch assembly 238 mounted to the wall panel 234. The wall panel 234 may have been previously secured to a wall structure 239, and so the LED switch assembly 238 is contemplated to be a simple replacement/retrofit for mechanical switches and the like that may have been installed therein.

The LED switch assembly 238 includes the centrally mounted LED switch device 10*f*, as well as a backlit status indicator 240. As indicated above, the LED switch device 10*f* may include the first electroluminescent semiconductor die 28*a*, which may have a red colored illumination. Further, the second electroluminescent semiconductor die 28*b* may have a green colored illumination. By way of example, the two colors may be utilized as an indicator of which one of the fans or the lights are to be controlled by any inputs received on the LED switch device 10*f* in that state. For instance, a red color illumination may indicate that the lamps 230 will be controlled, while a green color illumination may indicate the fan unit 229 will be controlled. Swiping a finger from the first segment 172 to the 174 is representative of decreasing power, which in the case of the lamp unit 233 being controlled, dims the illumination level thereof. In the case of the fan unit 229 being controlled, the rotation speed of the electric motor 226 is lowered. The more the touch remains on the second segment 174, the further the lighting is dimmed/motor speed is reduced. Swiping the finger in the opposite direction from the second segment 174 to the first segment 172 may cause an increase in brightness/speed. Tapping both the first segment 172 and the second segment 174 quickly may result in the lamp unit 233 or the fan unit 229 being turned on or turned off at once. Pressing and holding both the first segment 172 and the second segment 174 may switch the control mode from the lamp unit 233 to the fan unit 229, and vice versa. These control sequences can be programmed on the data processing device 60 as a set of executable instructions of detected inputs and generated responses. Although a specific control sequence has been described, it will be appreciated that any other control sequences may be implemented as different instructions that are executed by the data processing device 60.

Figure 11:
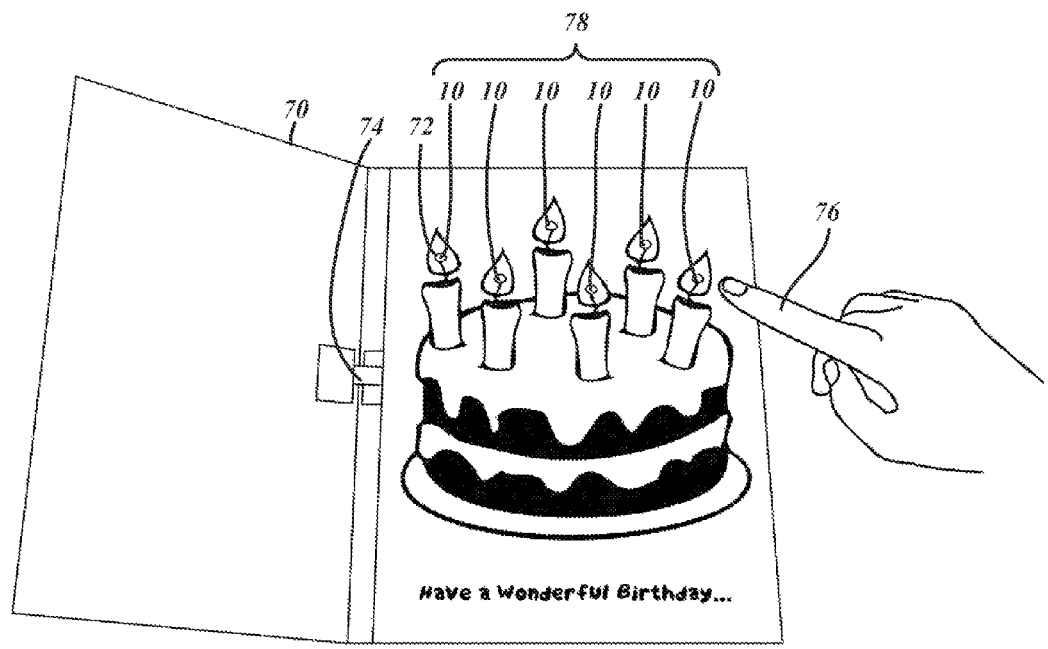
FIG. 11 shows one exemplary use of an array of LED switch devices in an interactive greeting card.

Another application of the LED switch device 10 is shown in FIG. 11, which is a greeting card 70 that includes a printed depiction of a cake with candles. The card 70 defines cutouts 72 through which the LED switch devices 10 are shown, and correspond to the location of the depicted candle flames. Thus, the illuminated LED switch devices 10 are intended to mimic the appearance of lit candles. Alternating colors may be utilized for different LED switch devices 10. Initially, all of the LED switch devices 10 may be illuminated upon opening the card 70 via a contact switch 74. The recipient's fingers can be passed over the LED switch devices 10 for deactivation, thereby simulating the "blowing out" of the candles. In general, this embodiment illustrates the use and basic configuration of an array 78 of LED switch devices 10 that are each controlled by the LED driver source based upon inputs received by the touch input controller 58.

Varying operating patterns are possible with the greeting card 70. It is contemplated that the LED switch devices 10 have at least two electroluminescent semiconductor dies 28 with one for the red color, and the other for either a blue or a green color. When the greeting card 70 is first opened, all of the LED switch devices 10 may be turned on with the red color, and optionally flashing. A simple musical score may be generated, and the recipient's fingers can be passed over the LED switch devices 10 to activate the secondary color of the electroluminescent semiconductor die 28. Thus, with the red and the blue colors activated, there is a pink colored resultant output, while with the red and green colors activated, there is a yellow colored resultant output. The activation sequence may be recorded while the musical score is playing, and that sequence may be replayed after a delay or after the music score concludes. Without the recording functionality, touching the LED switch devices 10 may be operative to activate the secondary color.

Figure 12:
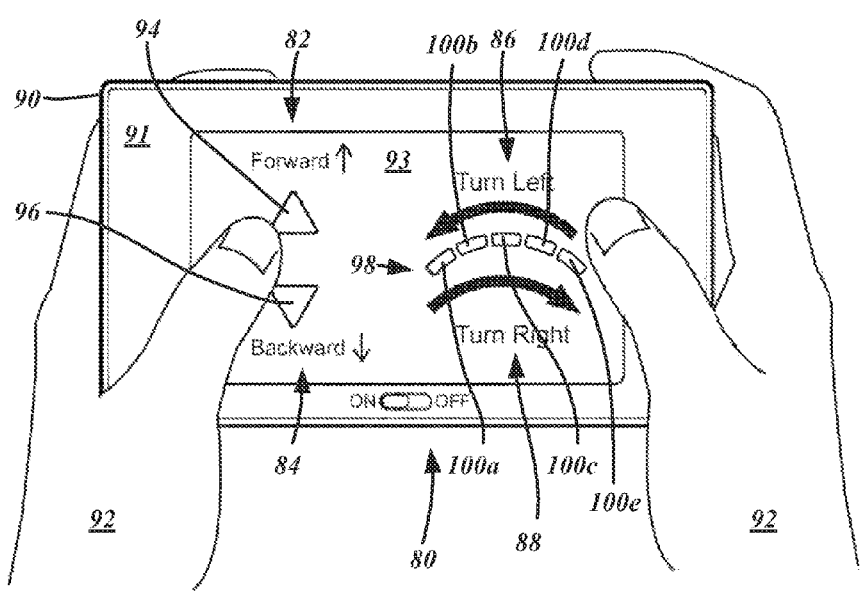
FIG. 12 shows another exemplary use of multiple LED switch devices in a remote controller, a top view thereof being illustrated.
Figures 1, 13A:
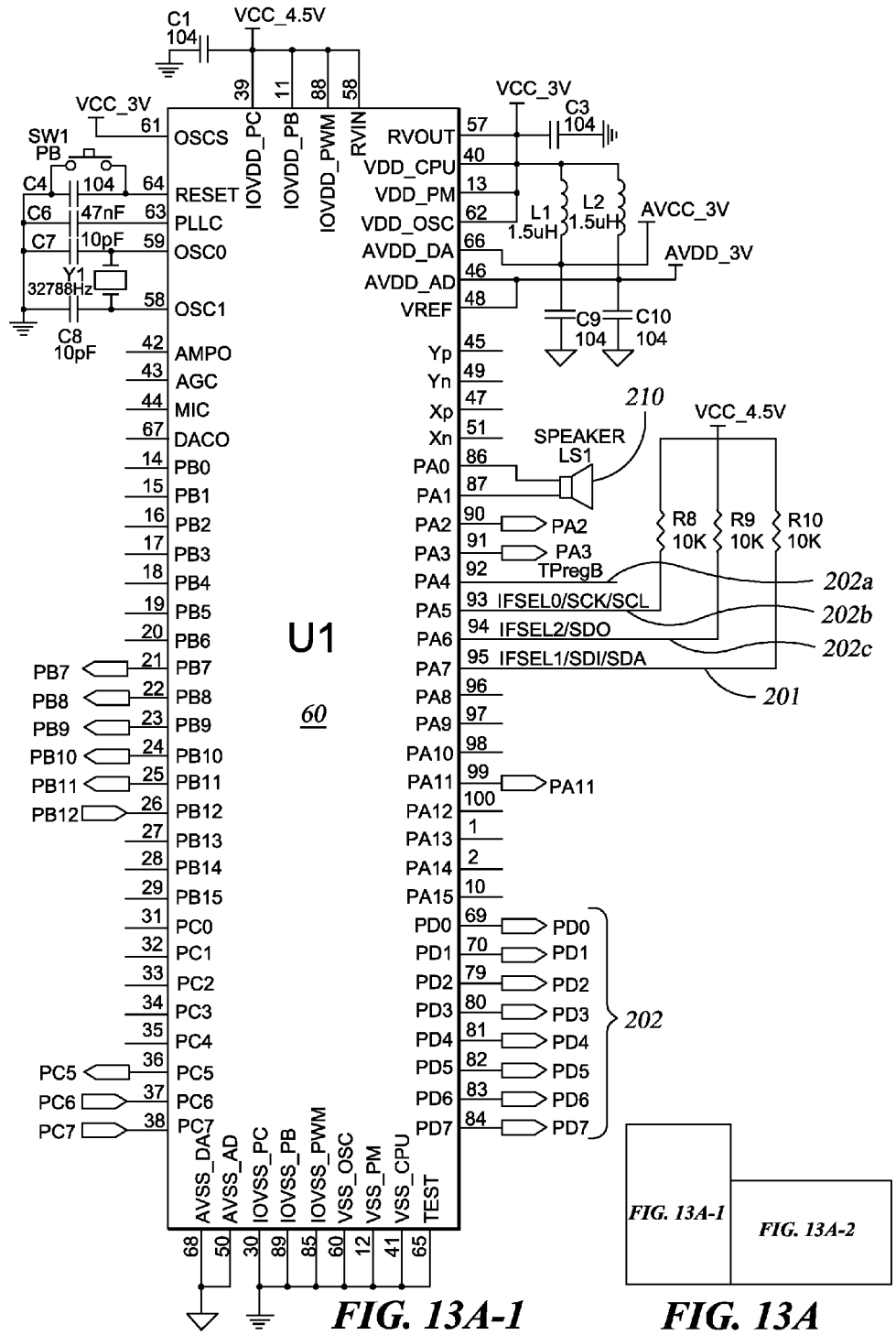
Figures 2, 13A:
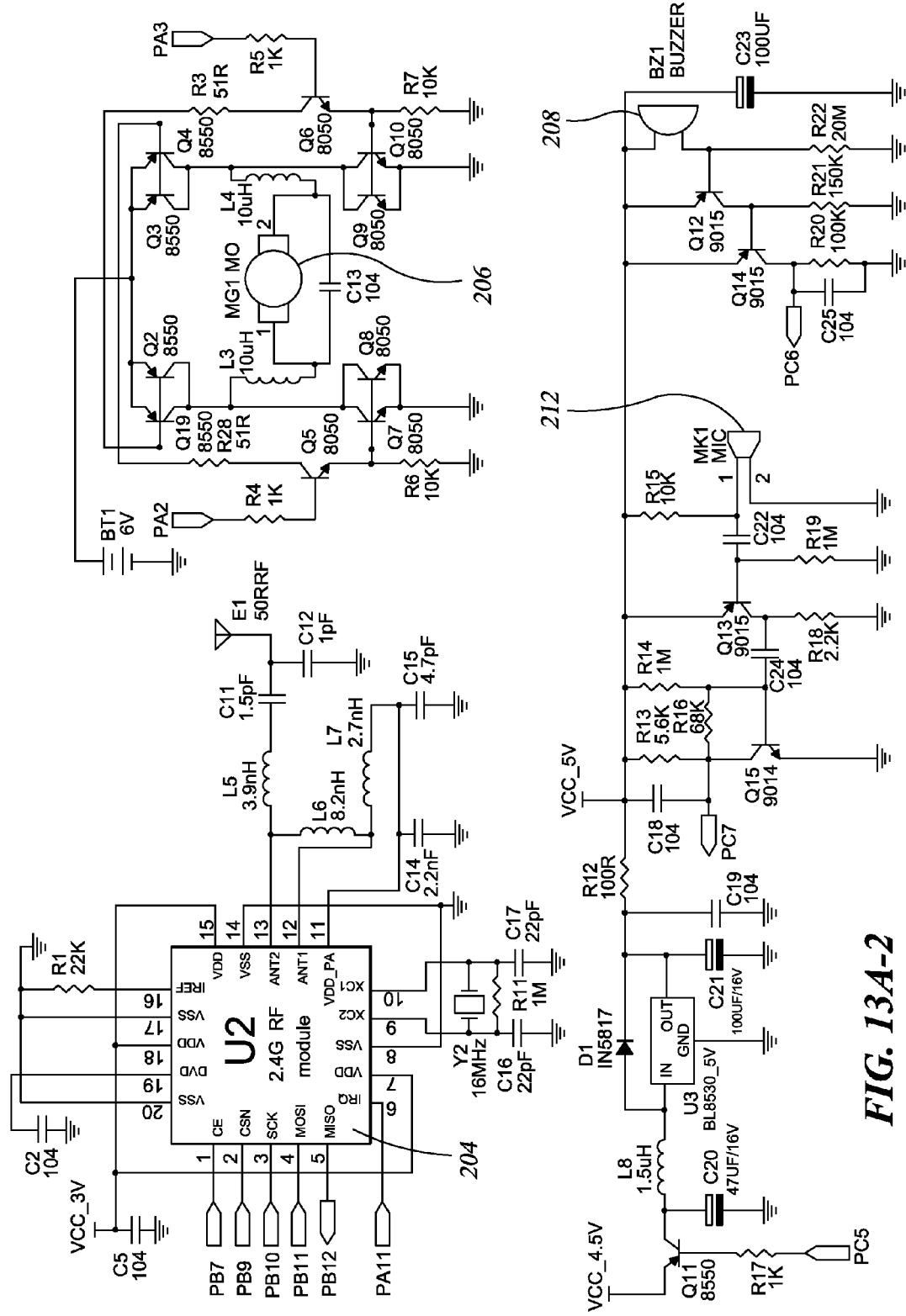
Figures 2, 13B:
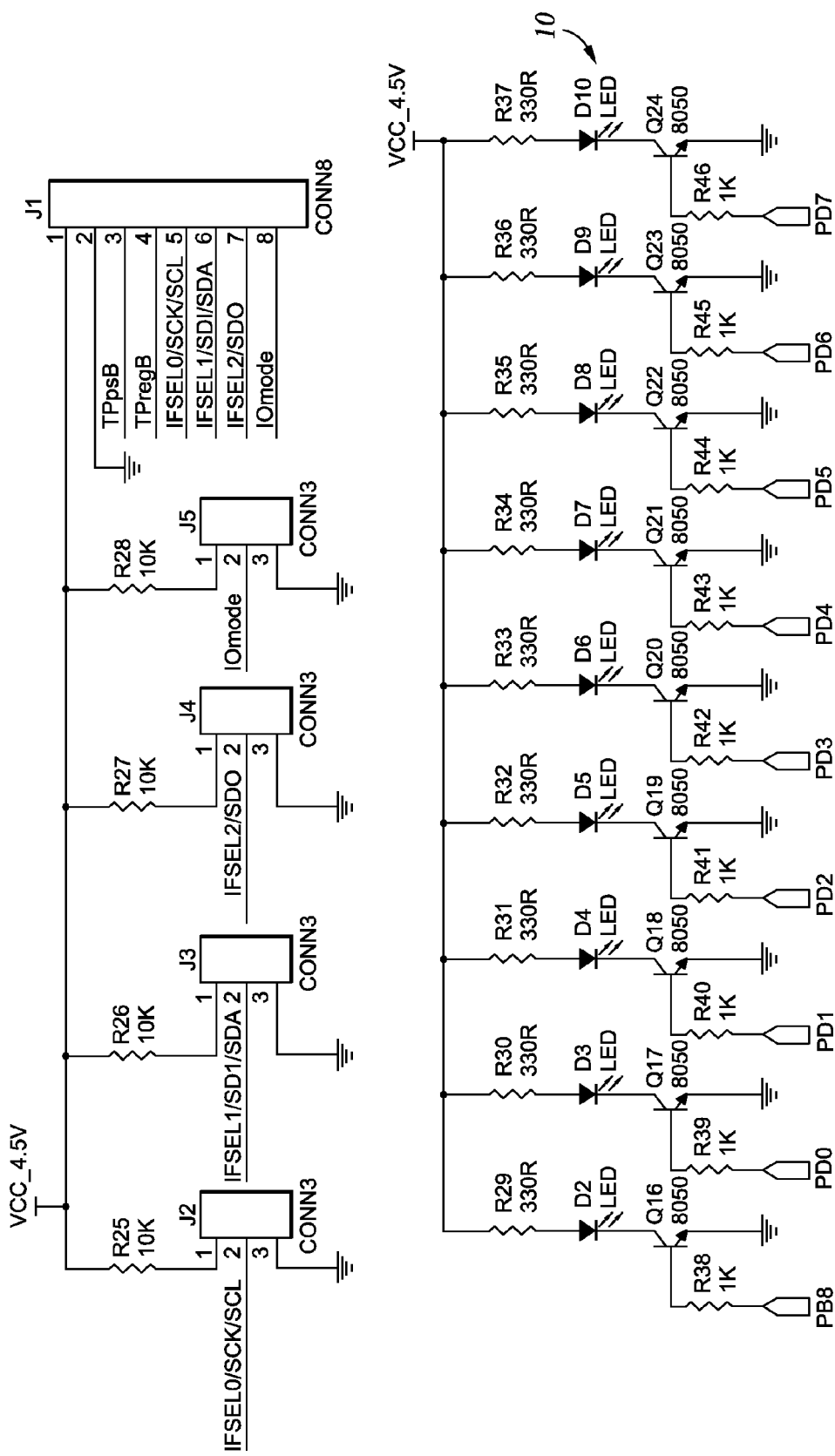

FIG. 12 shows another application of the LED switch devices 10 in a remote controller 80, which generally has inputs corresponding to a forward direction 82, an opposed reverse direction 84, a leftward direction 86, and a rightward direction 88. The remote controller 80 is comprised of a case 90 held within the hands 92 of the user. The case 90 and has a generally flat front surface 91, including a transparent or translucent Mylar sheet or film 93 overlaid on the LED switch devices 10. The sheet 93 may have various symbols and characters imprinted thereon that variously represent the functionality that can be invoked by the underlying LED switch devices 10. It will also be recognized that the sheet 93 may have transparent or semi-transparent portions, and opaque portions corresponding to the imprinted symbols and characters. An underlying opaque base sheet with cutouts may be provided.

For the forward direction 82, there is a single forward direction LED switch device 94, and for the reverse direction 84, there is a single reverse direction LED switch device 96, both of which are mounted underneath the sheet 93 of the case 90. By positioning the fingers over the LED switch devices 94, 96, a signal representative thereof can be generated and transmitted to a base receiver via radio frequency.

For the sideways directions 86, 88, there is an array 98 comprised of a first LED switch device 100a, a second LED switch device 100b, a third LED switch device 100c, a fourth LED switch device 100d, and a fifth LED switch device 100e. Each of these LED switch devices 100 are mounted underneath the sheet 93, and may have different emission colors. The degree of turning is variable, and depends on which of the five LED switch devices 100 is activated by positioning the fingers over the same. Alternatively, the rate at which the finger is swept from left to right or vice versa may determine the degree of turning exhibited by the receiving device.

The remote controller 80 can be used as a control modality for a number of interactive systems, including radio-controlled vehicles and toys, video games, and so forth. As illustrated above, the inputs provided can be simple on/off, and various degrees of input can be provided by utilizing an array of multiple LED switch devices 10.

In relation to its functions, the remote controller 80 is understood to have a similar basic architecture as described above with reference to the block diagram of FIG. 7. With reference to the schematic diagram of FIG. 13A-1, FIG. 13A-2, FIG. 13B-1, and FIG. 13B-2, there is a microcontroller or data processing device 60. As briefly noted above, the data processing device 60 is configured to execute a series of preprogrammed instructions that generates certain outputs based upon provided inputs. The data processing device 60 is understood to have an arithmetic logic unit, various registers, an instruction decoder, and a control unit, as is typical of data processing devices. An internal random access memory may also be included, as well as read-only memory that is used to pre-store frequently utilized data such as speech and movement sequences. By way of example, the programmable data processing device 60 is 16-bit digital signal processing (DSP) integrated circuit. One commercially available option is the eSL Series IC from Elan Microelectronics Corporation of Hsinchu, Taiwan, though any other suitable IC devices may be readily substituted.

In further detail, the data processing device 60 has at least one input port 201 and a plurality of output ports 202. The output ports 202 are connected to the LED switch devices 10 as well as the touch input controller 58, as will be detailed below. In the illustrated embodiment, the anode of the electroluminescent semiconductor device is connected to power, while its cathode is connected to a collector of a transistor. The base of the transistor is connected to the output port 202 of the data processing device 60; thus, when the transistor is biased on by a high voltage generated on the output port 202, the electroluminescent semiconductor (and hence the LED) is turned on. On the other hand, when the transistor is biased off by a low voltage on the output port 202, the LED is turned off.

The touch sensor leads 15 of the LED switch device 10 are connected to the touch input controller 58, which detects capacitance changes as indicated above. Upon detection, a corresponding signal is generated as an output, which is passed to the input port 201 of the data processing device 60, labeled as PA7. In further detail, the data processing device 60 communicates with the touch input controller 58 over the Serial Peripheral Interface (SPI) inter-device communications modality. Thus, being a serial communications system, a single data input port 201 is utilized. A first output port 202a for the chip select line (TPreg) is connected to the touch input controller 58 (and specifically pin 4 thereof) for indicating to the touch input controller 58 that the data processing device 60 is ready to receive data. Furthermore, second output port 202*b*, designated for the serial clock line (SCK) is also connected to the touch input controller 58 (and specifically pin 21 and 24 thereof) to provide a clock synchronization signal. A third output port 202*c* for the serial data out line (SDO) is connected to pin 20 of the touch input controller 58, and this is understood to be for purposes of compliance with the master-slave arrangement as dictated by the SPI standard. The signal to the input port 201, designated as the serial data in line (SDI) is connected to pin 22 of touch input controller 58, and is contemplated to include data relating to the identity of the LED switch device 10 upon which an input was detected, and so forth. Other data relating to the functioning of the touch input controller 58 may be communicated as well.

It is contemplated that the data processing device 60 is programmed with executable instructions that generate specific outputs to the output ports 202 and reflected in the LED switch devices 10 connected thereto, in response to inputs from the touch input controller 58 that are generated upon a detected touch on the LED switch devices 10. Thus, certain LEDs can be turned on or off when touched, as discussed above in relation to the greeting card 70. Furthermore, the functionality provided by the remote controller 80 with respect to the activation and deactivation of the on-board LEDs are implemented by the data processing device 60.

Various other functionalities are contemplated for the remote controller 80. As briefly mentioned above, the remote controller 80 can transmit instructions to a base receiver. Such data transmission functions are handled by a radio frequency transceiver integrated circuit 204. The operating frequency thereof is understood to be around 2.4 GHz, though any others may be substituted. Along these lines, RF transmission is not necessary, and other wireless or wired transmission modalities may be substituted. In addition to data transmission, the remote controller 80 includes a force feedback feature enabled by a motor 206 that is also connected to the data processing device 60. Similarly, sound output is generated through a piezoelectric buzzer 208 and/or a loudspeaker 210. If desired, sound inputs can be provided to the data processing device 60 through the piezoelectric buzzer 208 and/or a microphone 212.

Figure 14:
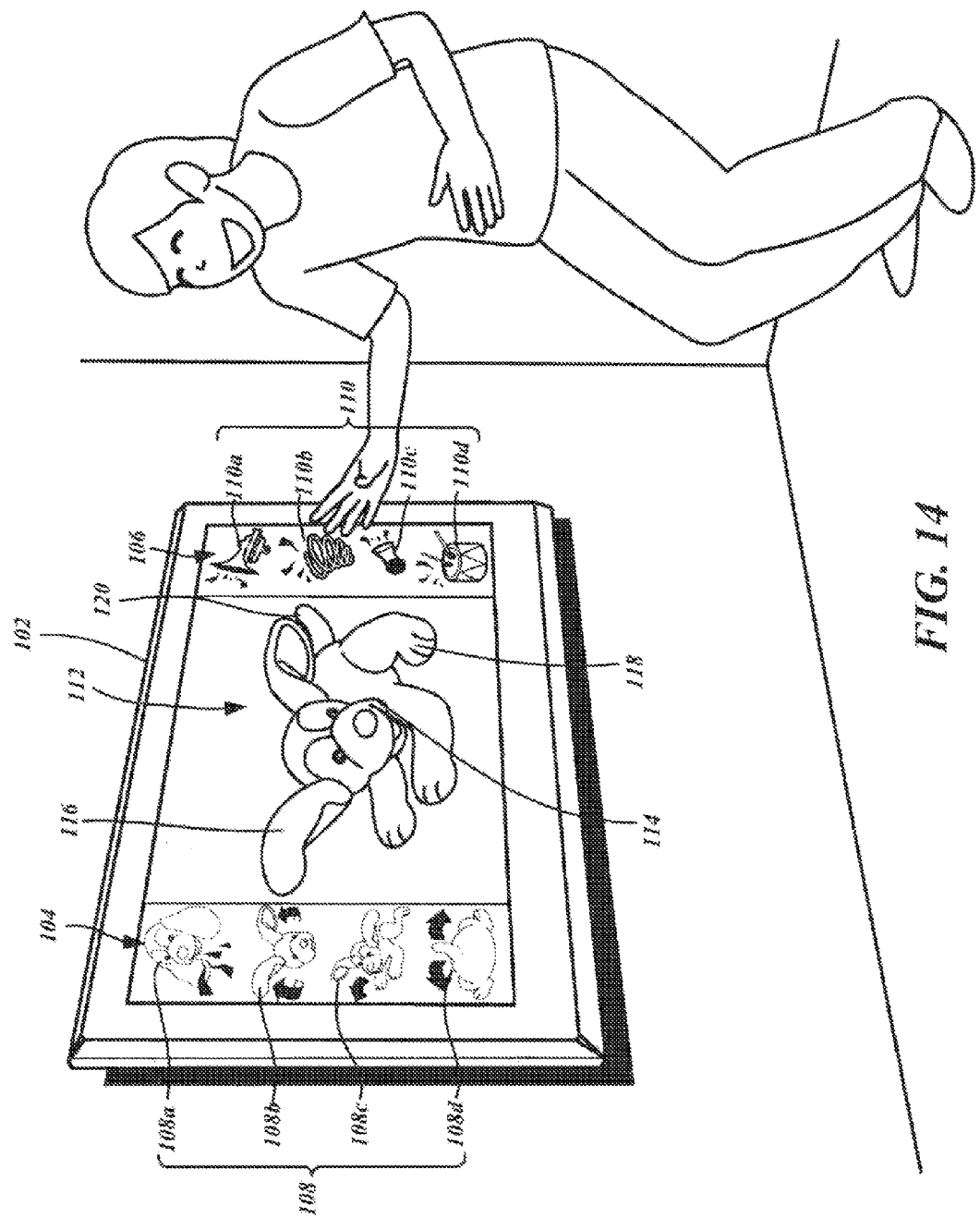
FIG. 14 shows a large array of LED switch devices that comprise an interactive LED display panel.

The application of the LED switch devices 10 is understood to be scalable. With reference to FIG. 14, a wall-mounted LED display panel 102 is comprised of rows and columns of LED switch devices 10 capable of emitting a wide range of colors across the visible spectrum. The LED display panel 102 is configured to display images by activating and deactivating the LED switch devices 10 with particular colors and intensities. By way of example, the interface shown on the LED display panel 102 is segregated into a left column 104 and a right column 106, which include icons 108, 110, respectively.

Selecting one of the icons 108 in the left column 104 is understood to select a specific animation of a feature of a character 112 displayed on the LED display panel 102. As utilized herein, the selection or touching of one of the icons 108 is understood to refer to placing a body part on or in close proximity to one or more LED switch devices 10 in the LED display panel 102 that correspond to those outputting that specific one of the icons 108. In one contemplated sequence, touching a first left column icon 108*a* activates the animation of a mouth 114, while touching a second left column icon 108*b* activates the animation of ears 116. Touching a third left column icon 108*c* activates the animation of legs 118, and selection of a fourth left column icon 108*d* activates the animation of a tail 120. Upon touching any of the icons 108, visual feedback is provided by placing an emphasis thereon, such as by, for example, highlights.

Touching one of the icons 110 in right column 106, on the other hand, is understood to select a particular output sound signal. Touching a first right column icon 110*a* is understood to generate a trumpet sound, and touching a second right column icon 110*b* generates a "spring" or "boing" type sound. Furthermore, touching a third right column icon 110*c* generates a bike horn sound, while touching a fourth column icon 110*d* generates a drum sound.

Figure 15:
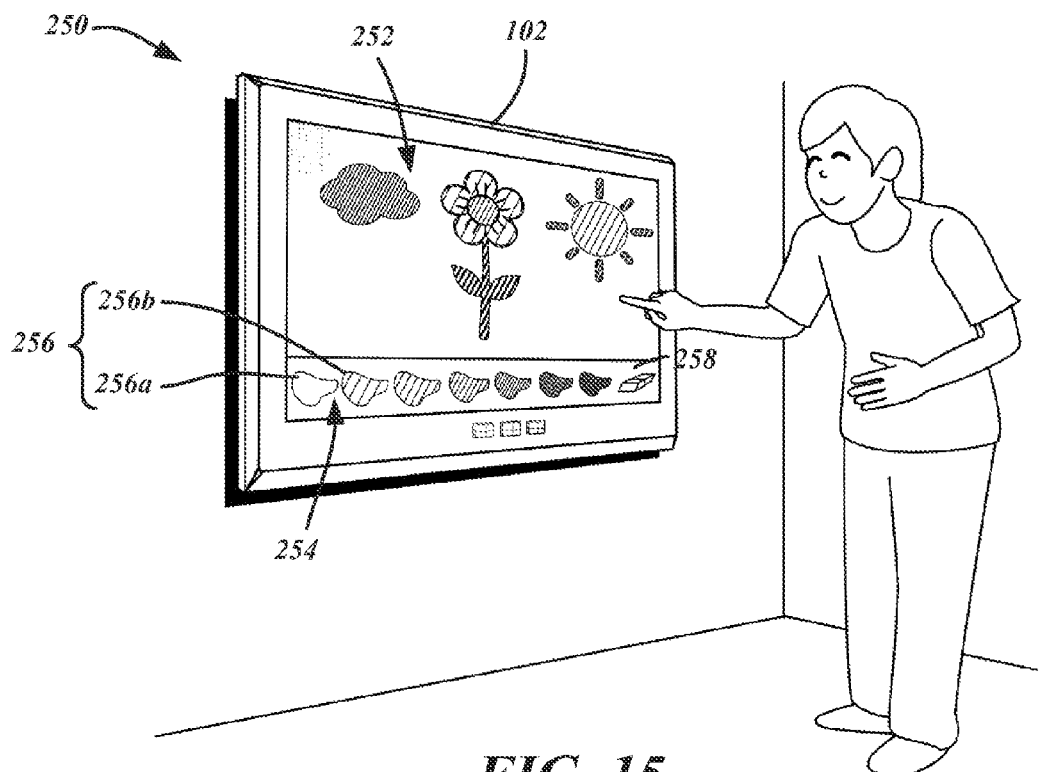
FIG. 15 shows the LED display panel comprised of a large array of LED switch devices utilized in a picture drawing interface.

In another embodiment illustrated in FIG. 15, the LED display panel 102 may be configured as picture drawing interface 250. As indicated above, the LED display panel 102 is an array of LED switch devices 10 arranged in rows and columns, and can emit a wide range of colors across the visible spectrum. Again, various images can be displayed by activating and deactivating certain LED switch devices 10. In the contemplated picture drawing interface 250, the screen area is segregated into an upper drawing board section 252 and a lower color palette section 254 that displays a series of icons 256, with each having a different color. Thus, it is contemplated that the lower palette section 254 resembles a conventional artist's color palette. Selection of one of the icons 256 is understood to select that corresponding color for use, as will be described in further detail below.

Touching a first color icon 256*a* allows the user to "draw" on the drawing board section 252 in the selected color. That is, when the user touches or comes into close proximity with a particular LED switch device(s), then that one will be illuminated with the selected color. It is contemplated that selecting a second color icon 256*b* will change the drawing color with the newly selected color. Again, as the user touches or comes into close proximity with a particular LED switch device(s), it will be illuminated with such color. In addition, there may be an eraser icon 258 that, when selected, alters the response of the touched LED switch devices 10 to deactivate rather than activate with a selected color when the color icon 256 is otherwise selected or activated. Variations on standard touch inputs are possible as mentioned above, and in the present context of the picture drawing interface 250, holding the erase icon 258 for a predetermined length of time may deactivate the entirety of the LED display panel 102. The LED display panel 102 can be further miniaturized for enhanced portability.

Figure 16:
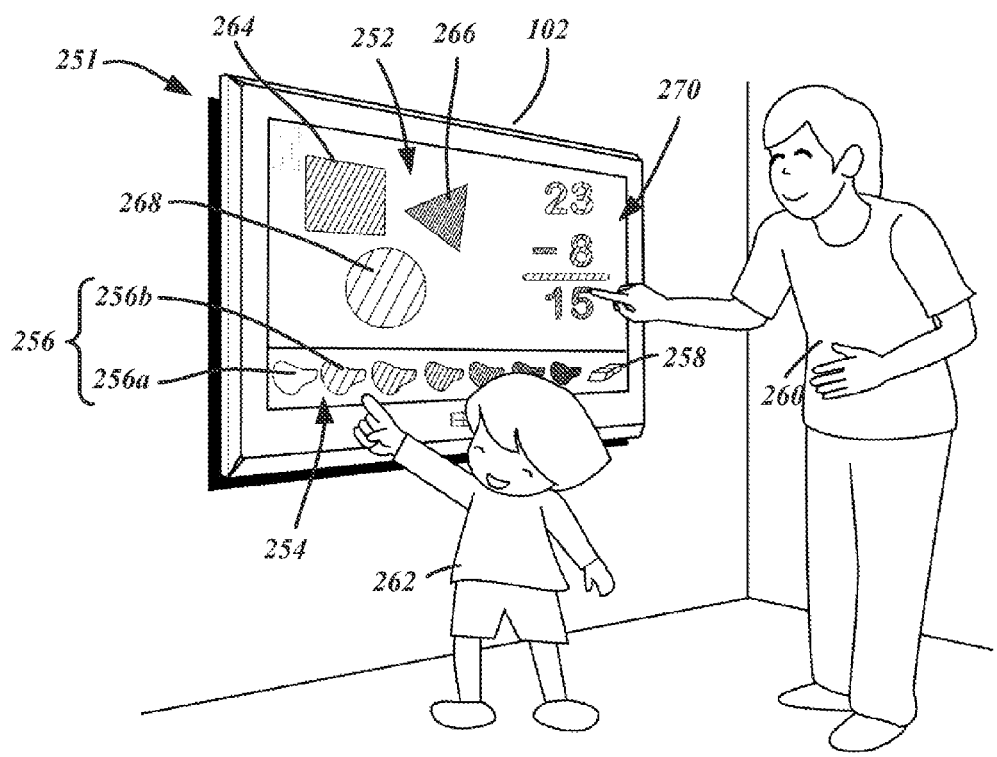
FIG. 16 shows the LED display panel utilized in an interactive teaching interface.

In the particular exemplary embodiment shown in FIG. 16, a teacher 260 may utilize the LED display panel 102 in a classroom as an interactive teaching interface 251 to instruct a student 262 visually on a variety of different subjects. For instance, the concepts of shapes and colors may be taught by directing the student 262 to draw different shapes in different colors, including a rectangle 264 in a first color, a triangle 266 in a second color, and a circle 268 in a third color.

Additionally, the student 262 may be taught about words, letters, and numbers by drawing such characters on the display panel 102. For further functionality, it is possible to connect the LED display panel 102 to a data processing device, such that a software application capable of character recognition may be executed thereby. Based upon the inputs on the LED display panel 102, the letters and words represented by certain sequence of inputs may yield responsive outputs. By way of example only and not of limitation, such outputs may be the pronunciation of inputted and recognized letters and words. In the case of mathematics instruction, the numbers and/or formulas 270 being drawn on the LED display panel 102 may be verified or corrected, with appropriate sound and visual outputs being generated upon a correct or incorrect input. Such sound outputs may include a "cheering" sound when correct, or an "uh-oh" exclamation when incorrect. Thus, the interactive teaching interface 251 engages both the teacher and the student to greatly enhance teaching effectiveness and learning enjoyment.

It will be appreciated that numerous educational and entertainment applications are possible.

Although only a moderately sized LED display panel 102 on the order of a human body is illustrated in FIGS. 14, 15, and 16, larger ones that span the entirety of walls and the like are also envisioned. It is understood that the graphics generated on such panels 102 may be varied considerably, as are the way such graphics are generated in response to various types of user input. Furthermore, the LED display panel 102 may be utilized as a remote control or an interface for larger conventional LED display panels, where the input and the responses generated on the LED display panel 102 are transmitted to the larger display panel to be displayed.

Other, more sophisticated play patterns utilizing the LED switch device 10 are also envisioned. With reference to FIG. 17A, an anthropomorphized interactive bear doll 122 has a body section 124, a pair of legs 126, a pair of arms 128, and a head 130. As will be appreciated, the interactive doll 122 may portray humans, other animals besides a bear such as dogs, cats, rabbits, birds and the like, or any other character real or imagined. Along these lines, the foregoing features of the interactive doll 122 are presented by way of example only, and not of limitation.

Figure 18:
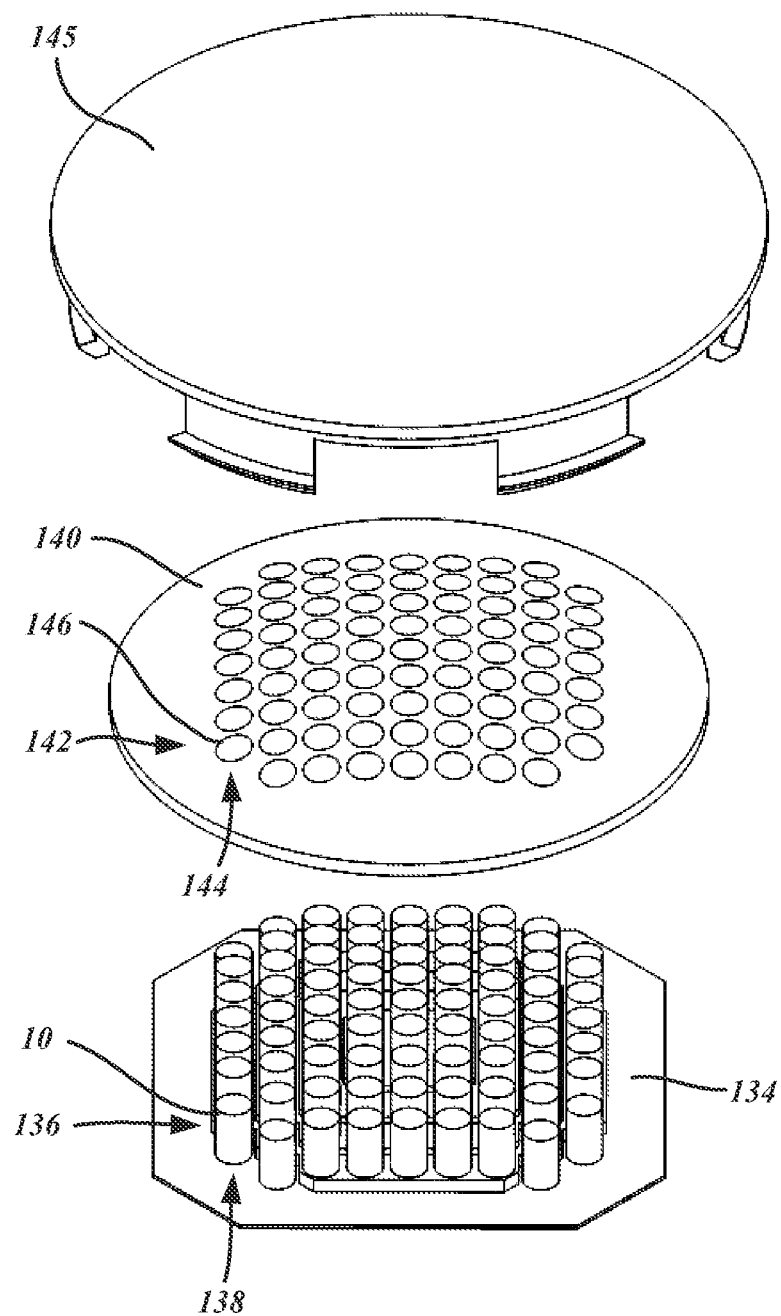
FIG. 18 is an exploded perspective view of an array assembly utilized in the interactive doll of the present disclosure shown in FIGS. 17A and 17B.
Figures 1, 19A:
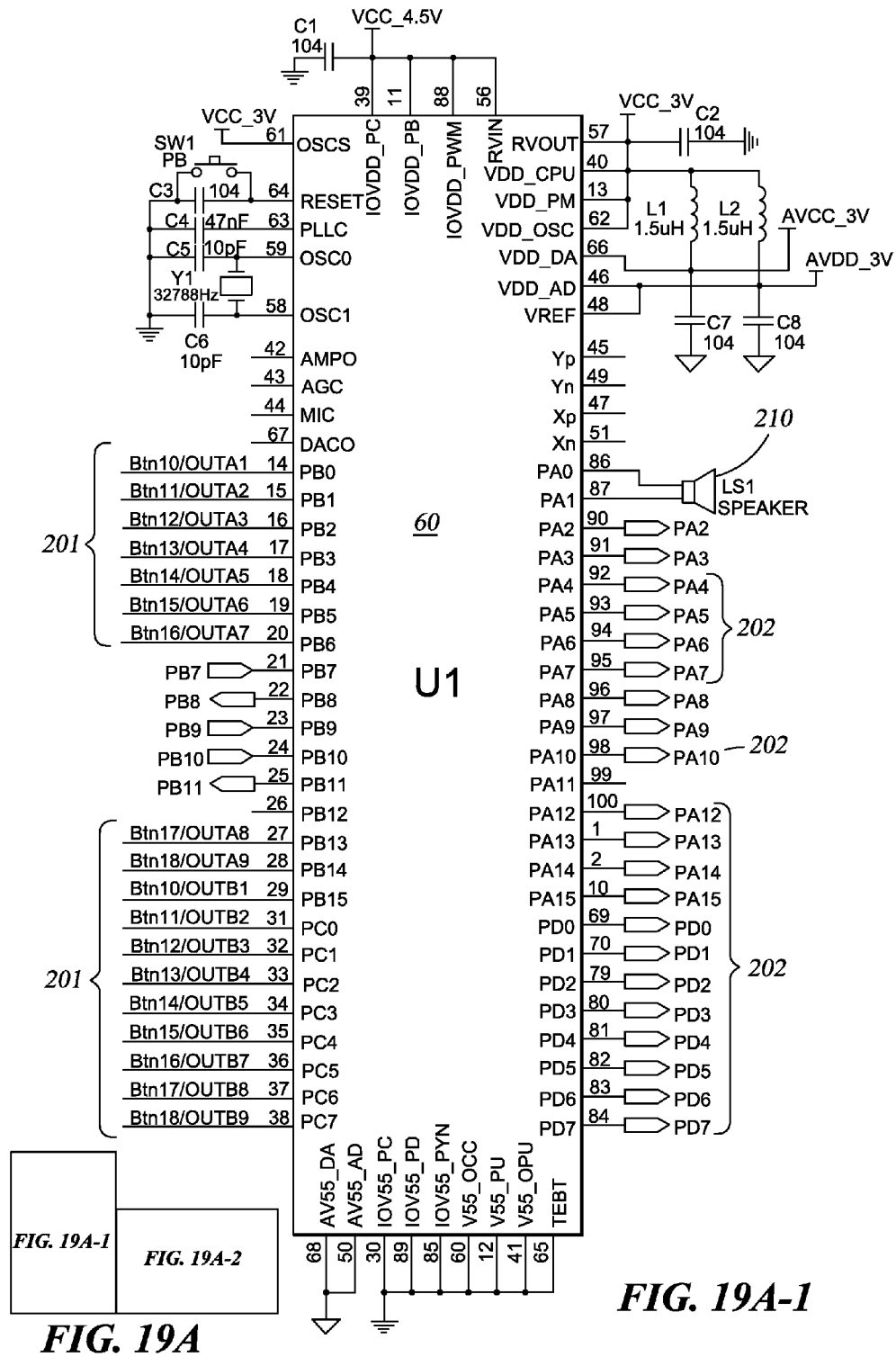
Figures 2, 19A:
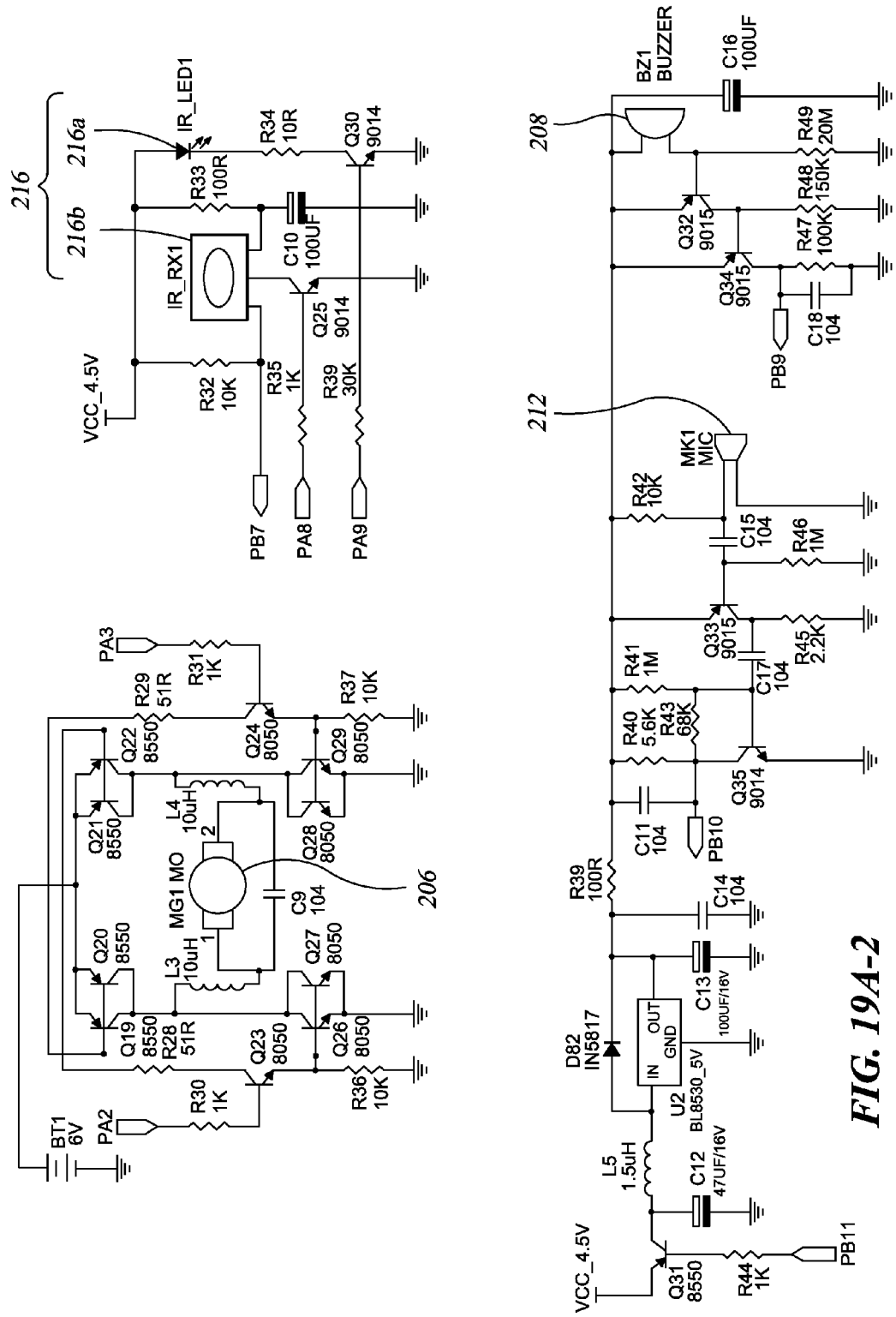
Figures 1, 19B:
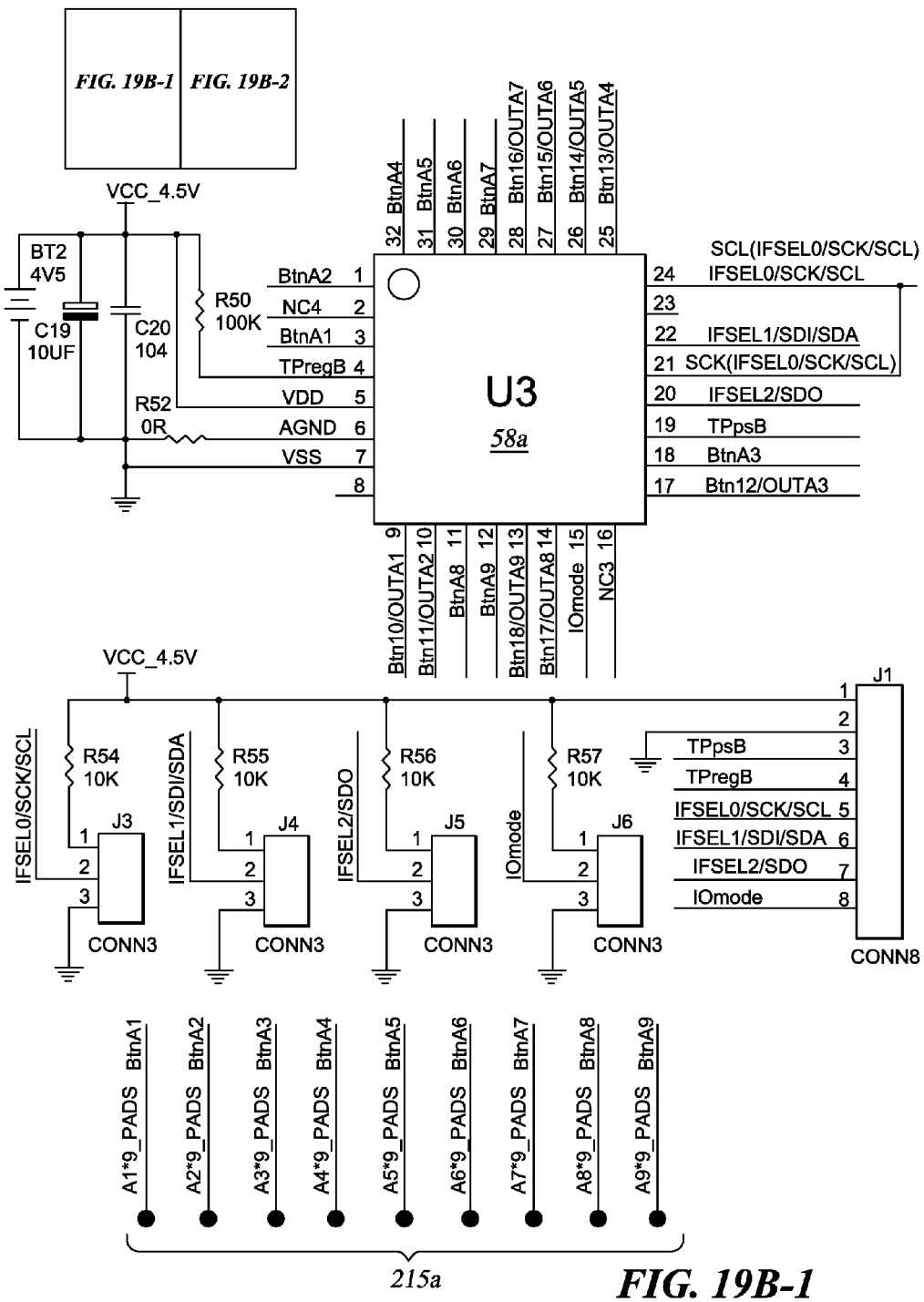
Figures 2, 19B:
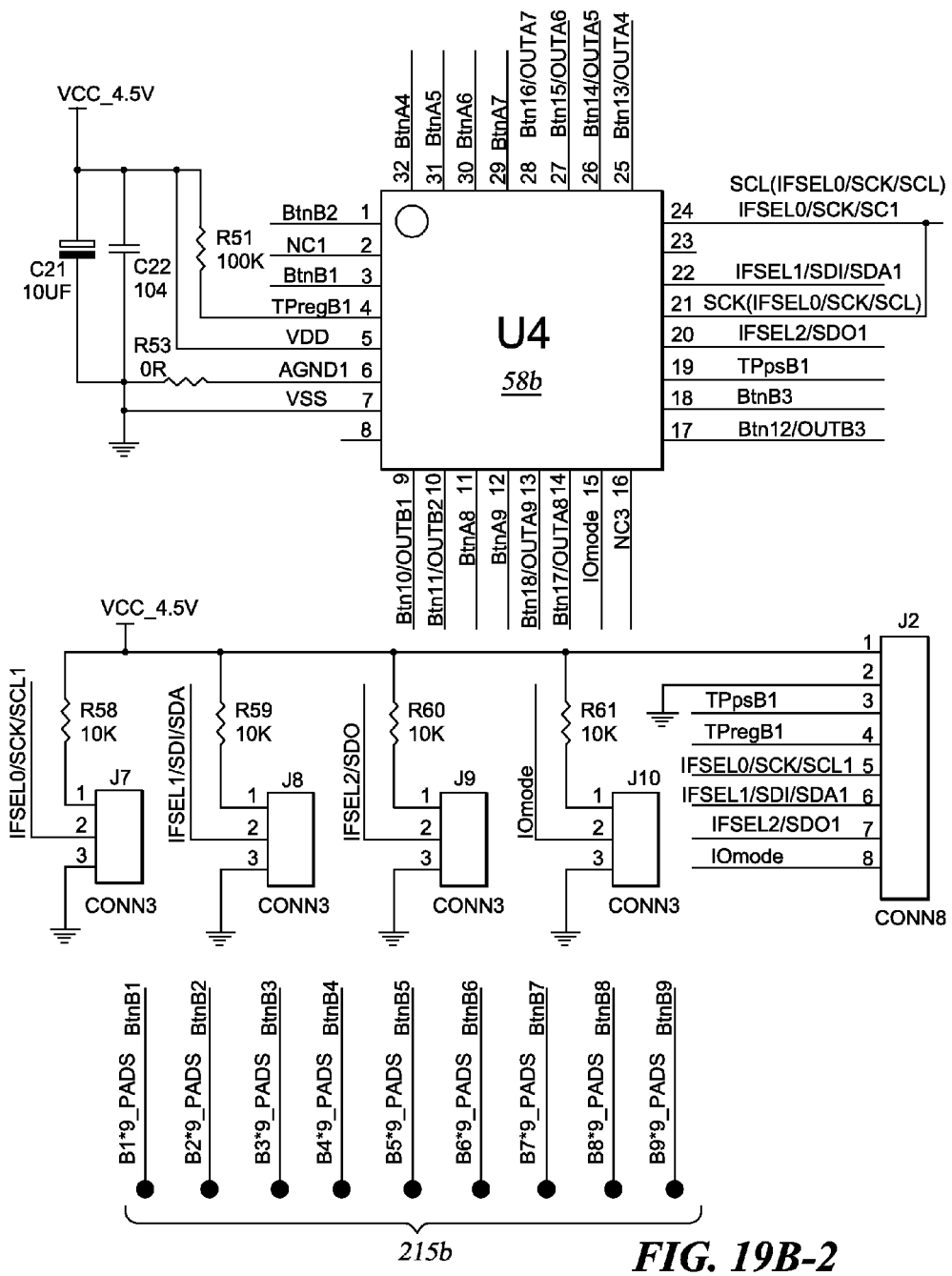
Figure 19C:
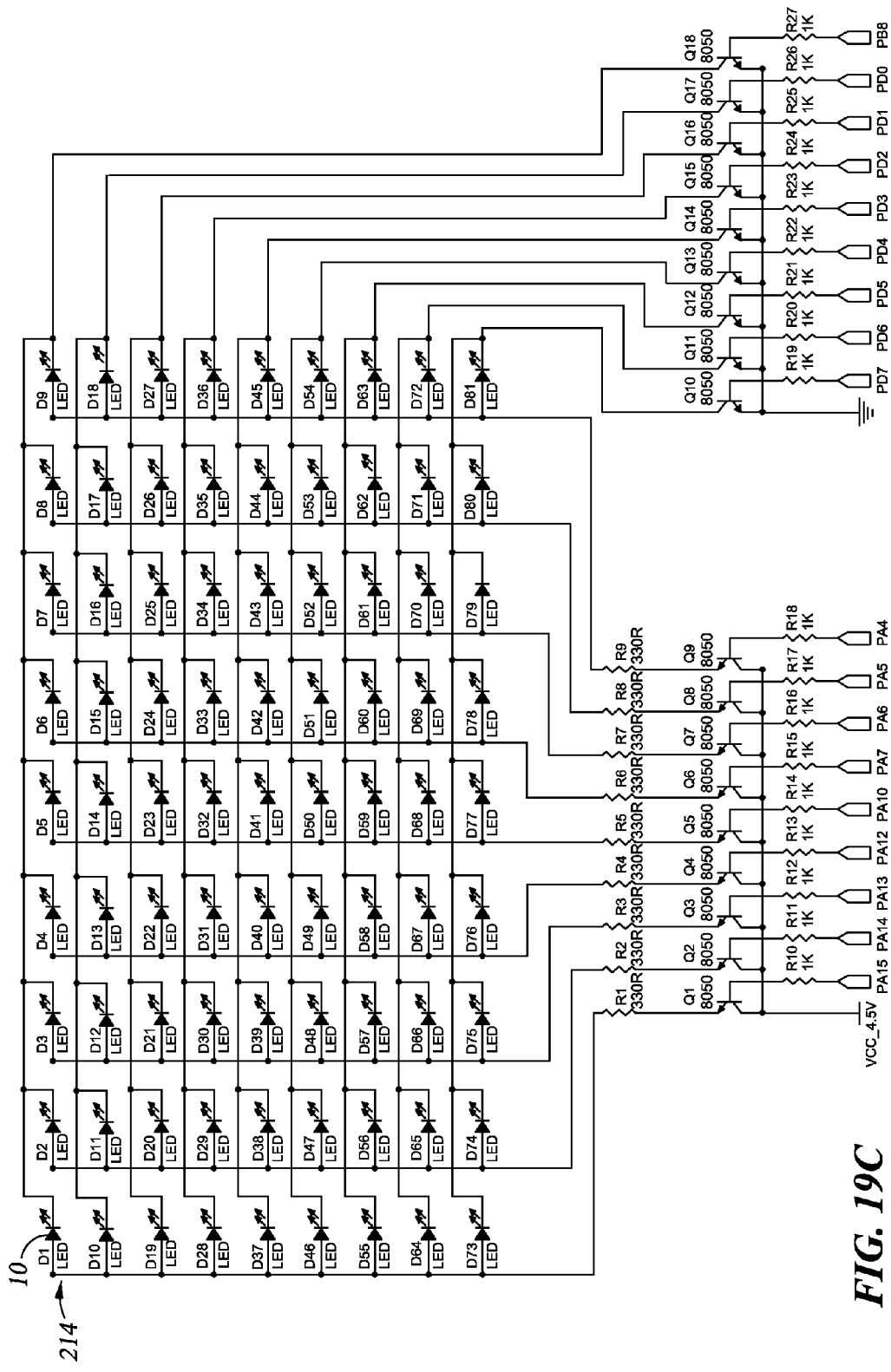

The body section 124 of the doll includes a matrix assembly 132 with individual LED switch devices 10. In further detail illustrated in FIG. 18, the matrix assembly 132 includes a printed circuit board 134 upon which the LED switch devices 10 are mounted in a series of rows 136 and columns 138. As shown, one LED switch device 10 from each of the four corners of the matrix is omitted, so in sum, there are 77. The heights of the centrally disposed LED switch devices 10 may be higher than those peripherally disposed, so as to define a generally spherical outline. A light guide 140 that similarly define rows 142 and columns 144 of holes that correspond to the position of the LED switch devices 10 is mounted on to the printed circuit board. It is understood that the light guide 140 directs the light emission. Mounted onto the light guide 140 and the matrix of LED switch devices 10 is a spherical top cover 145 that is contour-matched.

Other ways of constructing the matrix assembly 132 are also known. One low-cost technique involves mounting and/or etching the respective cathode lead frame anvils 16, anode lead frame posts 20, touch sensor lead frame 23, electroluminescent semiconductor dies 28, and the touch sensor contacts 39 onto respective sides and layers of the printed circuit board 134 in the aforementioned matrix pattern. Thereafter, the electroluminescent semiconductor dies 28 are wire bonded so that the respective cathode lead frame anvils 16 and anode lead frame posts 20 are electrically connected to the respective cathode contact 30 and anode contact 32 of electroluminescent semiconductor dies 28. The entire matrix may then be encapsulated into a single case. The details of this process, as well as others, will be recognized by those having ordinary skill in the art.

Figure 17B:
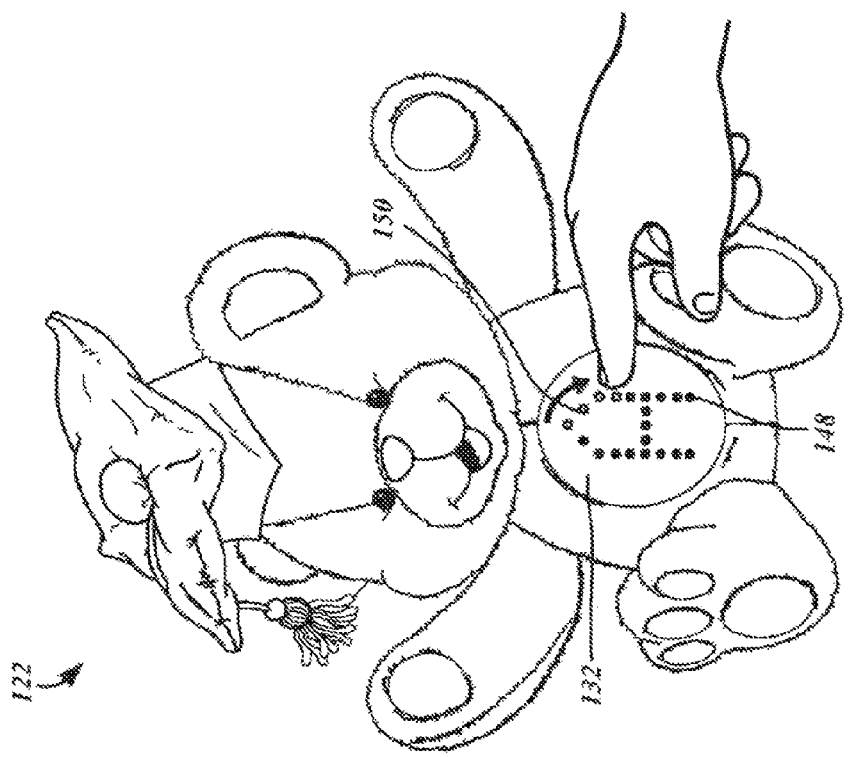
FIGS. 17A and 17B show an interactive doll that includes an array of LED switch devices.
Figure 17A:
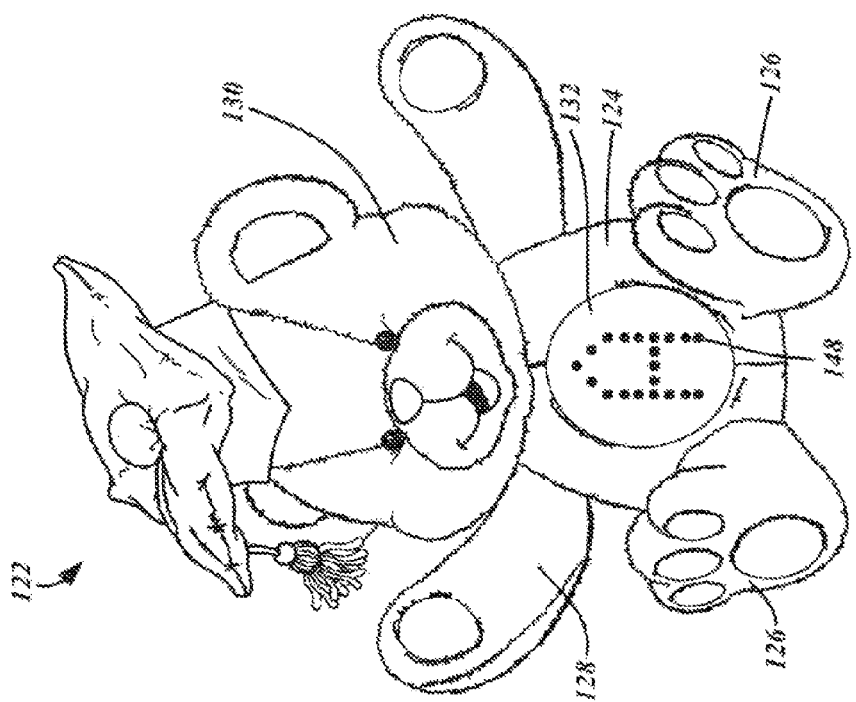

With reference to FIG. 17A and FIG. 17B, one of many possible play patterns with the interactive doll 122 will now be considered. As particularly shown in FIG. 17A, the pattern begins with generating a line drawing 148 of a letter, a number, a shape, or an object on the LED switch device matrix. For this phase, the illumination may be a single color. Thereafter, a loudspeaker can emit a sound that signals the player to trace the lines of the pattern with his or her finger, or an otherwise capacitive component, in accordance with the sequence as appearing on the matrix.

Referring specifically to FIG. 17B, the user can trace along the lines, and as the finger traces or covers the specific LED switch devices 10 that were originally illuminated, those can change to a different color, as depicted in the changed LED switch devices 150. As the user progresses, further audible encouragement is generated to complete the pattern. Upon successfully completing the tracing of the pattern and a detection of the same, the loudspeaker can emit a congratulatory message and generate various lighting effects therefor. Again, it will be appreciated that this sequence has been presented by way of example only and not of limitation. Other play patterns are also deemed to be within the purview of those having ordinary skill in the art.

The interactive doll 122 is understood to have a similar basic architecture as described above. More particularly, as shown in the schematic diagrams of FIG. 19A-1, FIG. 19A-2, FIG. 19B-1, FIG. 19B-2, and FIG. 19C, the interactive doll 122 includes is the microcontroller or data processing device 60 with a plurality of input ports 201 and a plurality of output ports 202. The output ports 202 are connected to the LED switch devices 10, which are arranged as a matrix 214 of 9×9 (−4), or 77 individual ones.

A first set of the touch sensor leads 215*a*, which are part of each LED switch device 10 in the matrix 214, are connected to a first touch input controller 58*a*, while a second set of touch sensor leads 215*b*, which are also a part of each LED switch device 10 in the matrix 214, are connected to a second touch input controller 58*b*. As noted above, the touch input controller 58 detects capacitance changes on the respective touch sensor contacts 39. Upon detection, a representative signal is generated as an output, which is connected to the input ports 201 of the data processing device 60. In some embodiments however, the touch input controller 58 can be incorporated into the data processing device 60. In further detail, the data processing device 60 is programmed with executable instructions that generate specific outputs to the output ports 202 based on certain inputs, particularly in implementing the above-described play pattern.

The audible outputs generated by the interactive doll 122 are through either the piezoelectric buzzer 208 and/or the loudspeaker 210. One or more motors 206 can be mechanically linked to the legs 126, arms 128, or the head 130 to animate the same. In addition to the foregoing, the interactive doll 122 has additional functionality such as data transmission that, for example, is handled by an infrared transceiver 216, including a transmitter 216*a* and a receiver 216*b*.

Figure 20:
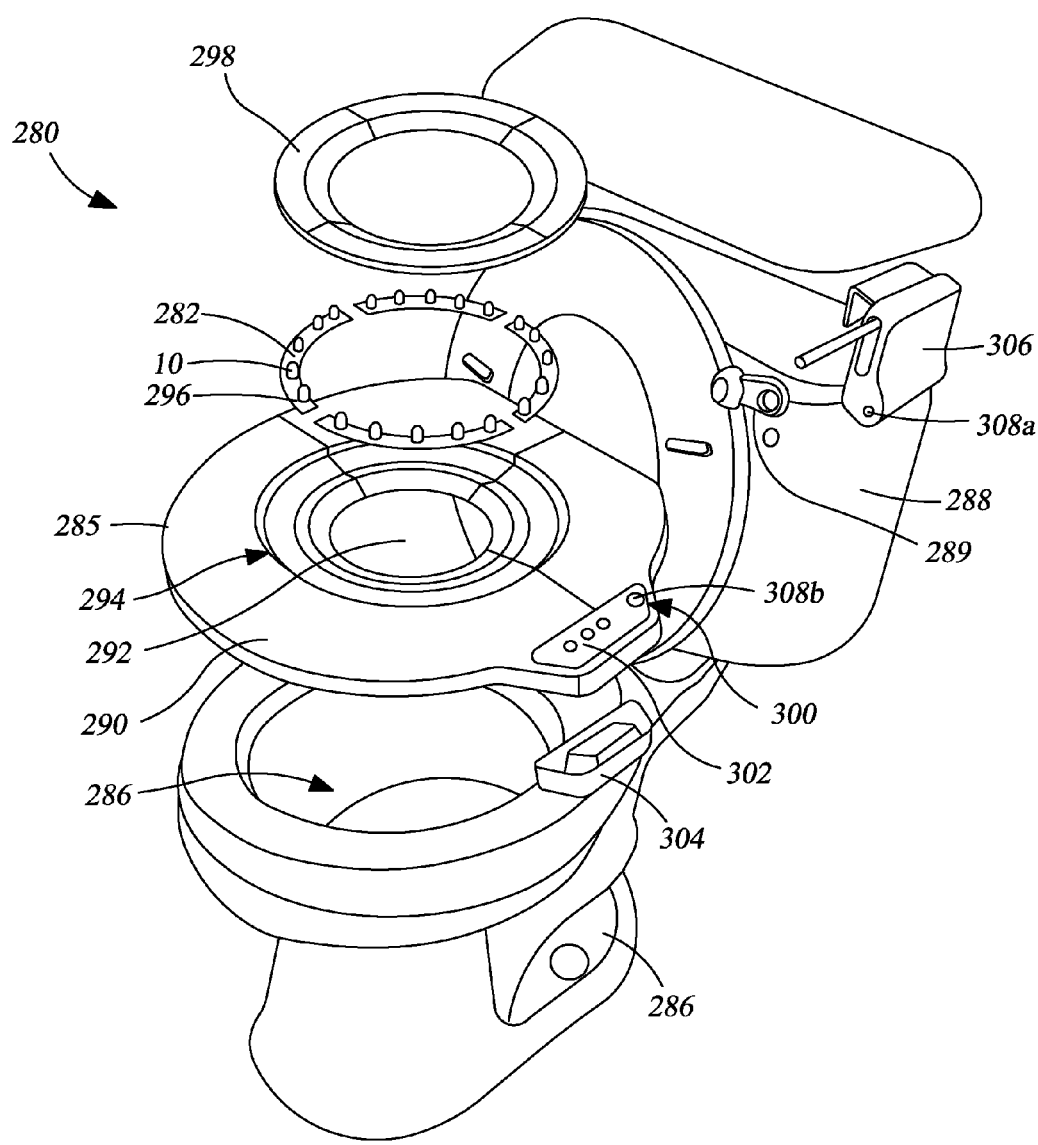
FIG. 20 is an exploded view of a disinfecting device utilizing an array of LED switch devices.

The above-described applications of the LED switch device 10 have involved visible spectrum wavelength emissions therefrom. It need not be limited, however, and even emissions of wavelengths in the ultraviolet spectrum are also contemplated. With reference to FIG. 20, there is a sanitizing device 280 with another embodiment of an ultraviolet LED switch device array 282. As will be recognized, ultraviolet radiation can be utilized to sterilize, sanitize, and disinfect a variety of surfaces, and the presently contemplated sanitizing device 280 is suitable therefor.

For contextual purposes, one known surface prone to bacteria, viruses, and the like is a toilet 284. More particularly, the toilet 284 includes a bowl 286 in which various waste matter may be deposited. The toilet 284 may include a seat 285 fitted over the bowl 286 such that a separate contact surface is available for use. Water held in a tank 288 is utilized to flush the waste matter in the bowl 286 into the sewage system after a flush handle 289 is depressed. Unfortunately, as part of the flushing process, miniscule droplets of water containing bacteria and viruses may be ejected upwardly and outwardly from the bowl, thereby contaminating the outer surfaces of the toilet 284, including the seat 285. As a result, the seat 285 may serve as a modality by which contaminants are transferred to its user.

The seat 285 has a flat rim portion 290 with a hole 292 defined within a center section thereof. An inner periphery 294 of the flat rim portion 290 has a countersunk configuration, within which the ultraviolet LED switch device arrays 282 are mounted. In further detail, each of the ultraviolet LED switch device arrays 282 may include one or more LED switch devices 10 that are mounted on a printed circuit board 296 that is semi-circular in shape. The LED switch devices 10 therein are understood to have one or more electroluminescent semiconductor dies 28 that are capable of emitting an ultraviolet wavelength. A ring cover 298 is secured to the seat 285, and thereby enclosing the ultraviolet LED switch device arrays 282. It is contemplated that the ring cover 298 is constructed of a transparent epoxy or poly-resin, though any other suitably durable material may be utilized. A side portion 300 includes a control panel 302 as well as a battery compartment 304 that contains the energy source for driving the ultraviolet LED switch device arrays 282.

Various automation features may be implemented by the control panel 302. With a capacitive source touching or coming into proximity with the ring cover 298 and the ultraviolet LED switch device arrays 282, that input may be received and processed by the control panel 302, which may then activate the ultraviolet radiation. Furthermore, with a loss of the capacitive source (the user has left), the control panel may signal a flush handle automation unit 306 to actuate the flush handle 289 without user intervention. This signaling may be achieved with a pair of complementary infrared (IR) transceiver modules 308a and 308b associated with a respective one of the flush handle automation unit 306 and the control panel 302.

Figure 21A:
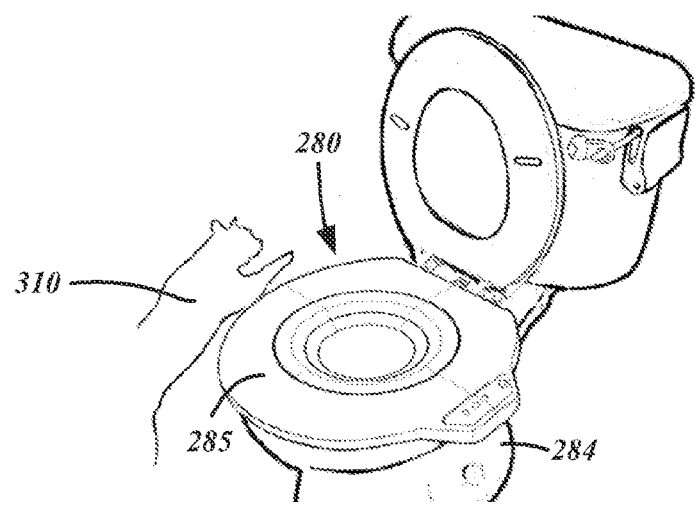
FIGS. 21A, 21B, and 21C show the disinfecting device shown in FIG. 20 in various states of use.
Figure 21B:
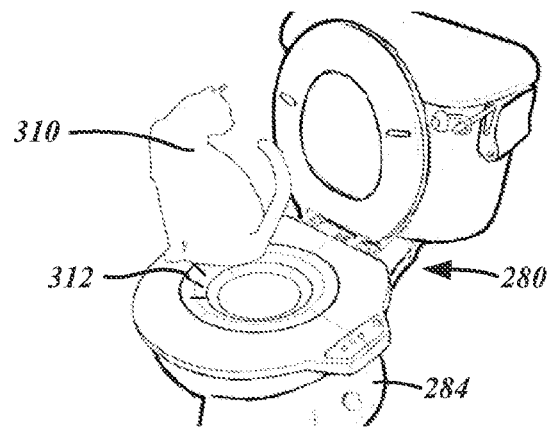
Figure 21C:
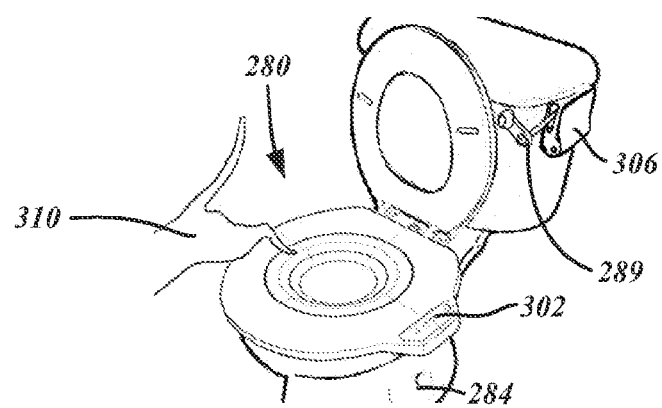

As best illustrated in FIGS. 21A-21C, and as particularly shown in FIG. 21A, a capacitive source 310 approaches the toilet 284 and the seat 285 thereof. At this point, the LED switch devices 10 are not activated to emit an ultraviolet radiation, and no inputs to the control panel 302 by way of the capacitive touch sensing has been tripped. FIG. 21B shows the capacitive source 310 on the seat 285. Thus, the touch sensor contacts of the LED switch devices 10 will exhibit a change in capacitance and indicating the same to the control panel 302. In response, the LED switch devices 10 may be activated to emit the ultraviolet radiation 312, disinfecting the capacitive source 310. With the departure of the capacitive source 310 as shown in FIG. 21C, the touch sensor contacts of the LED switch devices 10 no longer indicates an input to the control panel 302, and the ultraviolet emissions may be stopped. At the same time, the flush handle automating unit 306 may trigger the flush handle 289 to flush the toilet 284 and expel any matter that may have been deposited into the bowl 286.

Alternatively, actuating the flush handle 289 may activate a transmission to the control panel 302 to turn on the LED switch devices 10. As indicated above, the flushing action may have deposited contaminants onto the surface of the seat 285.

It will be recognized that while the capacitive source 310 shown in FIGS. 21A-21C is depicted as a pet cat, any other capacitive source such as humans may be substituted. Along these lines, while a particular embodiment of the sanitizing device 280 that utilizes the LED switch device array has been described, it may take any other suitable form.

Various applications of the contemplated LED switch device 10 have been disclosed, including the room lighting dimmer switch 220, the interactive greeting card 70, the remote controller 80, the LED display panel 102, the interactive doll 122, and the sanitizing device 280. These have been presented by way of example only, and it will be appreciated that numerous other applications are possible.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present invention with more particularity than is necessary, the description taken with the drawings making apparent to those skilled in the art how the several forms of the present invention may be embodied in practice.

What is claimed is:

1. A touch input circuit, comprising:
 a light emitting diode switch device including:
  at least one electroluminescent semiconductor element with a first polarity contact and a second polarity contact;
  a first polarity lead electrically connected to the first polarity contact;
  a second polarity lead electrically connected to the second polarity contact;
  a first touch sensor structure of a unitary construction defined by a first touch sensor lead section, a first touch sensor contact section, and a first touch sensor lead frame section;
  a case encapsulating the electroluminescent semiconductor element, the first touch sensor contact section, and the first touch sensor lead frame section;
  wherein an entire structural contiguity of the first touch sensor lead frame section and the first touch sensor contact section are unexposed on an outer surface of the case, the first touch sensor contact section extending into the case with galvanic isolation of the first touch sensor lead frame section and the first touch sensor contact section being maintained relative to an exterior of the case while dielectric conduction from the exterior of the case to the first touch sensor lead frame section and the first touch sensor contact section is allowed;
 at least one touch input transmission line electrically connected to the first touch sensor lead section of the light emitting diode switch device;
 a touch input controller with an input that is singularly receptive to a capacitive touch input upon the light emitting diode switch device, a capacitive change to the first touch sensor contact section being conducted through an entire structural contiguity of the first touch sensor structure to the input of the touch input controller over the touch input transmission line.

2. The touch input circuit of claim 1, wherein the first touch sensor lead section is disconnected from the electroluminescent semiconductor element.

3. The touch input circuit of claim 1, wherein:
 the first polarity lead is a cathode to which a negative power supply voltage is applied as a negative common; and
 the second polarity lead is an anode.

4. The touch input circuit of claim 1, wherein:
the first polarity lead is an anode to which a positive power supply voltage is applied as a positive common; and
the second polarity lead is a cathode.

5. The touch input circuit of claim 1, further comprising:
a second touch sensor structure defined by a second touch sensor lead section, a second touch sensor contact section, and a second touch sensor lead frame section, the second touch sensor structure being electrically connected to an independent capacitive touch sensor controller input and singularly receptive to the first capacitive touch input, a capacitance change to the second touch sensor contact section in response to the first capacitive touch input being conducted through an entire structural contiguity of the second touch sensor structure; and
wherein an entire structural contiguity of the second touch sensor lead frame section and the second touch sensor contact section are unexposed on an outer surface of the case, the second touch sensor contact section extends into the case with galvanic isolation of the second touch sensor lead frame section and the second touch sensor contact section being maintained relative to an exterior of the case while dielectric conduction from the exterior of the case to the second touch sensor lead frame section and the second touch sensor contact section is allowed.

6. The touch input circuit of claim 1, wherein the case is a through-hole package.

7. The touch input circuit of claim 6, wherein the case is at least partially translucent.

8. A combination input and output device, comprising:
a light emitting diode driver integrated circuit including a plurality of independent output lines;
a capacitive touch input controller integrated circuit including a plurality of independent input lines;
a plurality of touch input transmission lines electrically connected to a respective one of the plurality of independent input lines; and
an array of light emitting diode switch devices, each device including:
at least one electroluminescent semiconductor element with a first polarity contact and a second polarity contact;
a first polarity lead electrically connected to the first polarity contact;
a second polarity lead electrically connected to the second polarity contact;
a first touch sensor structure defined by a first touch sensor lead section, a first touch sensor contact section, and a first touch sensor lead frame section, the first touch sensor structure electrically connected to an independent capacitive touch sensor controller input and singularly receptive to a capacitive touch input, a capacitance change to the first touch sensor contact section in response to the capacitive touch input being conducted through an entire structural contiguity of the first touch sensor structure to a single one of the plurality of independent input lines of the capacitive touch input controller over a corresponding single one of the plurality of touch input transmission lines; and
a case encapsulating the electroluminescent semiconductor element, the first touch sensor contact section, and the first touch sensor lead frame section, the first touch sensor contact section and the first touch sensor lead frame section being unexposed on an outer surface of the case, with galvanic isolation of the first touch sensor lead frame section and the first touch sensor contact section being maintained relative to an exterior of the case while dielectric conduction from the exterior of the case to the first touch sensor lead frame section and the first touch sensor contact section is allowed;
wherein the first touch sensor structure detects capacitive touch input that at least partially corresponds to a position within the array of the one of the light emitting diode switch devices on which the capacitive touch input was detected.

9. The combination input and output device of claim 8, further comprising:
a data processing device electrically connected to the capacitive touch input controller integrated circuit and the light emitting diode driver integrated circuit, the data processing device being programmed with executable instructions for generating outputs to the light emitting diode driver integrated circuit in response to inputs from the capacitive touch input controller integrated circuit.

10. A surface mount device (SMD) package light emitting diode switch device, comprising:
an SMD package carrier with an open top and an interior defined by a plurality of sidewalls and an interior floor opposed to the open top;
a plurality of leads extending outwardly from sidewalls of the SMD package carrier;
a first lead frame structurally contiguous and in electrical communication with a first one of the plurality of leads and laterally extending in the interior of the SMD package carrier in a parallel relationship to the interior floor and fixed at least partially within the SMD package carrier;
a second lead frame structurally contiguous and in electrical communication with a second one of the plurality of leads and laterally extending in the interior of the SMD package carrier in a parallel relationship to the interior floor and fixed at least partially within the SMD package carrier;
a first electroluminescent semiconductor element with a first polarity electrode and a second polarity electrode, the first electroluminescent semiconductor element being mounted on the first lead frame with the first polarity electrode being in electrical communication therewith, and a second polarity electrode being electrically connected to the second lead frame with the second polarity electrode being in electrical communication therewith;
a first touch sensor lead frame structurally contiguous and in electrical communication with a third one of the plurality of leads and laterally extending in the interior of the SMD package carrier in a parallel relationship to the interior floor and fixed at least partially within the SMD package carrier;
a first touch sensor contact in electrical communication with the first touch sensor lead frame, the first touch sensor contact extending in a substantially orthogonal relationship to the first touch sensor lead frame and the interior floor;
a partially translucent case enclosing the open top of the SMD package carrier, the first touch sensor contact and the electroluminescent semiconductor element being unexposed on an outer surface of the case, with galvanic isolation of the first touch sensor contact being maintained relative to an exterior of the case while dielectric conduction from the exterior of the case to the first touch sensor contact is allowed.

11. The SMD package light emitting diode switch device of claim 10, wherein the first electroluminescent semiconductor element and the first touch sensor contact are at least partially visibly unobstructed from the exterior of the case.

12. The SMD package light emitting diode switch device of claim 10, further comprising:
   a bond wire electrically connecting the second polarity electrode to the second lead frame.

13. The SMD package light emitting diode switch device of claim 10, further comprising:
   a third lead frame structurally contiguous and in electrical communication with a fourth one of the plurality of leads and laterally extending in the interior of the SMD package carrier, the third lead frame being in a parallel relationship to the interior floor and fixed at least partially within the SMD package carrier; and
   a second electroluminescent semiconductor element with a first polarity electrode and a second polarity electrode, the second electroluminescent semiconductor element being mounted on the third lead frame with the first polarity electrode being in electrical communication therewith, and a second polarity electrode being electrically connected to the second lead frame with the second polarity electrode being in electrical communication therewith;
   wherein the first electroluminescent semiconductor element emits a different color than the second electroluminescent semiconductor element.

14. The SMD package light emitting diode switch device of claim 10, wherein the first touch sensor contact, the first touch sensor lead frame, and the third one of the plurality of leads collectively define a single, unitary first touch sensor structure.

15. The SMD package light emitting diode switch device of claim 14, wherein the first touch sensor structure is electrically connected to a first independent capacitive touch sensor controller input.

16. The SMD package light emitting diode switch device of claim 10, wherein the plurality of sidewalls includes a first sidewall and an opposed second sidewall.

17. The SMD package light emitting diode switch device of claim 16, wherein:
   the first lead frame extends from an inner portion of the interior toward the first sidewall;
   the first one of the plurality of leads, with which the first lead frame is contiguous, extends outwardly from the first sidewall.

18. The SMD package light emitting diode switch device of claim 17, wherein:
   the second lead frame extends from an inner portion of the interior toward the second sidewall in an opposed relation to the first lead frame;
   the second one of the plurality of leads, with which the second lead frame is contiguous, extends outwardly from the second sidewall.

19. The SMD package light emitting diode switch device of claim 17, wherein:
   the touch sensor lead frame extends from an inner portion of the interior toward the second sidewall in an opposed relation to the first lead frame;
   the third one of the plurality of leads, with which the touch sensor lead frame is contiguous, extends outwardly from the second sidewall.

* * * * *